(12) United States Patent
Bissantz et al.

(10) Patent No.: US 8,044,202 B2
(45) Date of Patent: Oct. 25, 2011

(54) AZASPIRO DERIVATIVES

(75) Inventors: Caterina Bissantz, Village-Neuf (FR); Christophe Grundschober, Rodersdorf (CH); Raffaello Masciadri, Basel (CH); Hasane Ratni, Habsheim (FR); Mark Rogers-Evans, Oberwil BL (CH); Patrick Schnider, Bottmingen (CH)

(73) Assignee: Hoffmann-la Roche Inc., Nutley, NJ (US)

( * ) Notice: Subject to any disclaimer, the term of this patent is extended or adjusted under 35 U.S.C. 154(b) by 977 days.

(21) Appl. No.: 11/960,799

(22) Filed: Dec. 20, 2007

(65) Prior Publication Data

US 2008/0161333 A1 Jul. 3, 2008

(30) Foreign Application Priority Data

Dec. 29, 2006 (EP) ..................................... 06127334

(51) Int. Cl.
*A61K 31/438* (2006.01)
*C07D 401/04* (2006.01)

(52) U.S. Cl. ......................................... 546/18; 514/278
(58) Field of Classification Search ............... 546/18; 514/278
See application file for complete search history.

(56) References Cited

U.S. PATENT DOCUMENTS

| 2001/0039286 A1 | 11/2001 | Dinnell et al. |
| 2002/0052371 A1 | 5/2002 | Fukami et al. |

OTHER PUBLICATIONS

Dorwald F. A. Side Reactions in Organic Synthesis, 2005, Wiley: VCH, Weinheim p. IX of Preface.*
Ebner et al., (2002), Eur. J. Neurosci. vol. 15 pp. 384-388.
Bielsky et al., (2004), Neuropsychopharmacology, vol. 29 pp. 483-493.
Liebsch et al., (1995), Regulatory Peptides vol. 59 pp. 229-239.
Michelini et al., (1999), Annals NY Acad. Sci. vol. 897 pp. 198-211.
Van Kerckhoven et al., (2002) Eur. J. Pharmacol. vol. 449 pp. 135-141.
Delgado et al., J. Org. Chem., vol. 10, p. 2862-2866 (1993).

* cited by examiner

*Primary Examiner* — Rita Desai
(74) *Attorney, Agent, or Firm* — George W. Johnston; Patricia S. Rocha-Tramaloni; Kimberly J. Prior

(57) ABSTRACT

The present invention is concerned with novel indol-3-yl-carbonyl-azaspiropiperidine derivatives as V1a receptor antagonists, their manufacture, pharmaceutical compositions containing them and their use for the treatment of anxiety and depressive disorders and other diseases. In particular, the present invention is concerned with compounds of the general formula (I)

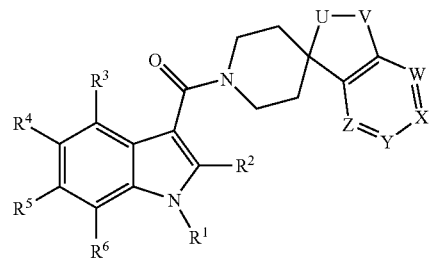

wherein $R^1$ to $R^6$, U, V, W, X, Y and Z are as defined in the specification.

20 Claims, No Drawings

AZASPIRO DERIVATIVES

PRIORITY TO RELATED APPLICATION(S)

This application claims the benefit of European Patent Application No. 06127334.8, filed Dec. 29, 2006, which is hereby incorporated by reference in its entirety.

BACKGROUND OF THE INVENTION

Vasopressin is a 9 amino acid peptide mainly produced by the paraventricular nucleus of the hypothalamus. Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water excretion and mediates the antidiuretic effects of vasopressin.

In the periphery vasopressin acts as a neurohormone and stimulates vasoconstriction, glycogenolysis and antidiuresis. In the brain vasopressin acts as a neuromodulator and is elevated in the amygdala during stress (Ebner, K., C. T. Wotjak, et al. (2002). "Forced swimming triggers vasopressin release within the amygdala to modulate stress-coping strategies in rats." *Eur J Neurosci* 15(2): 384-8). The V1a receptor is extensively expressed in the brain and particularly in limbic areas like the amygdala, lateral septum and hippocampus which are playing an important role in the regulation of anxiety. Indeed V1a knock-out mouse show a reduction in anxious behavior in the plus-maze, open field and light-dark box (Bielsky, I. F., S. B. Hu, et al. (2003). "Profound Impairment in Social Recognition and Reduction in Anxiety-Like Behavior in Vasopressin V1a Receptor Knockout Mice." *Neuropsychopharmacology*). The downregulation of the V1a receptor using antisense oligonucleotide injection in the septum also causes a reduction in anxious behavior (Landgraf, R., R. Gerstberger, et al. (1995). "V1 vasopressin receptor antisense oligodeoxynucleotide into septum reduces vasopressin binding, social discrimination abilities, and anxiety-related behavior in rats." *Regul Pept* 59(2): 229-39).

The V1a receptor is also mediating the cardiovascular effects of vasopressin in the brain by centrally regulating blood pressure and heart rate in the solitary tract nucleus (Michelini, L. C. and M. Morris (1999). "Endogenous vasopressin modulates the cardiovascular responses to exercise." *Ann N Y Acad Sci* 897: 198-211). In the periphery it induces the contraction of vascular smooth muscles and chronic inhibition of the V1a receptor improves hemodynamic parameters in myocardial infarcted rats (Van Kerckhoven, R., I. Lankhuizen, et al. (2002). "Chronic vasopressin V(1A) but not V(2) receptor antagonism prevents heart failure in chronically infarcted rats." *Eur J Pharmacol* 449(1-2): 135-41).

SUMMARY OF THE INVENTION

The present invention provides novel indol-3-yl-carbonyl-azaspiropiperidine derivatives as V1a receptor antagonists, their manufacture, pharmaceutical compositions containing them and their use for the treatment of anxiety and depressive disorders and other diseases.

In particular, the present invention provides compounds of formula (I)

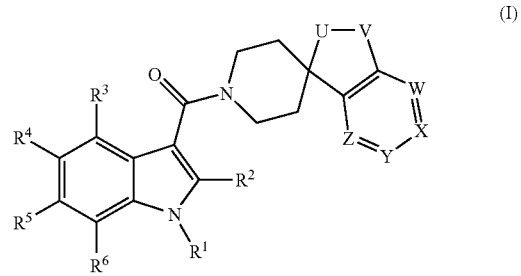

(I)

wherein
U is O, and V is $CH_2$,
U is O, and V is C=O,
U is $CH_2$, and V is O,
U—V is —CH=CH—,
U—V is —$CH_2$—$CH_2$—,
U is $CH_2$, V is $NR^7$;
U is C=O, and V is $NR^7$, or
U is C=O and V is O;
one or two of the variables W, X, Y and Z are nitrogen, the remaining variables being $CR^8$;
$R^1$ is H,
   $C_{11\text{-}12}$-alkyl, optionally substituted with CN or OH,
   $C_{1\text{-}6}$-haloalkyl,
   $C_{2\text{-}12}$-alkenyl,
   —$(CR^iR^{ii})_m$—$R^a$,
     wherein $R^i$ and $R^{ii}$ are independently from each other H, methyl, or ethyl;
     wherein m is from 0 to 4;
     wherein $R^a$ is
       phenyl, 5- to 6-membered heteroaryl, 3- to 7-membered heterocycloalkyl or 3 to 7-membered cyloalkyl,
         which are optionally substituted with one or more A, or
      —$NR^bR^c$, wherein $R^b$ and $R^c$ are each independently hydrogen,
       hydroxy,
       $C_{1\text{-}6}$-alkyl,
       —$S(O)_2$—$C_{1\text{-}6}$-alkyl, or
       —$C(O)$—$C_{1\text{-}6}$-alkyl,
   —$(CR^{iii}R^{iv})_n$—$C(O)R^d$,
     wherein $R^{iii}$ and $R^{iv}$ are independently from each other H, methyl, or ethyl;
     wherein n is from 0 to 4;
     wherein $R^d$ is
       $C_{1\text{-}6}$-alkoxy,
      —$NR^eR^f$, wherein $R^e$ and $R^f$ are each independently hydrogen,
       $C_{1\text{-}6}$-alkyl, or
       —$(C_{2\text{-}6}$-alkylene)-$NR^gR^h$; wherein $R^g$ and $R^h$ are each independently hydrogen, $C_{1\text{-}6}$-alkyl, or
       —$C(O)O$—$C_{1\text{-}6}$-alkyl, or
      phenyl, 5- to 6-membered heteroaryl, 3- to 7-membered heterocycloalkyl or 3 to 7-membered cyloalkyl,
        which are optionally substituted with one or more A,
   —$S(O)_2$-phenyl, wherein phenyl is optionally substituted with one or more halo, $C_{1\text{-}6}$-haloalkyl, $C_{1\text{-}6}$-alkyl, $C_{1\text{-}6}$-alkoxy, $C_{1\text{-}6}$-haloalkoxy, nitro, hydroxy or cyano;
   —$S(O)_2$—$C_{1\text{-}6}$-alkyl,
   —$S(O)_2N(C_{1\text{-}6}$-alkyl$)_2$, or
   —$S(O)_2NH(C_{1\text{-}6}$-alkyl);

A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —S(O)$_{0-2}C_{1-6}$-alkyl, nitro, hydroxy, cyano, —($C_{1-6}$-alkylene)-O—$C_{1-6}$-alkyl, —($C_{1-6}$-alkylene)-O—$C_{1-6}$-haloalkyl, —($C_{1-6}$-alkylene)-OR''', —C(O)O$C_{1-6}$-alkyl, —C(O)$C_{1-6}$-alkyl, —C(O)OR''', —C(O)R''', —C(O)NR'R'', —S(O)$_2$NR'R'', —(CH$_2$), —NR'R'', —(CH$_2$), —NR'C(O)—$C_{1-6}$-alkyl, —(CH$_2$), —NR'S(O)$_2$—$C_{1-6}$-alkyl, —(CH$_2$)$_x$—$C_{3-6}$-cycloalkyl, or —(CH$_2$)$_x$—R''',
wherein x is from 0 to 4,
R' and R'' are each independently H or $C_{1-6}$-alkyl, or
R' and R'' together with the nitrogen to which they are bound form a 5 or 6-membered heterocycle comprising one or two heteroatoms selected from N, O and S, and
R''' is phenyl or 5- to 6-membered heteroaryl, optionally substituted with one, two, or three halo, $C_{1-6}$-haloalkyl, $C_{1-6}$-alkyl, or $C_{1-6}$-alkoxy,
$R^2$ is hydrogen,
  $C_{1-6}$-alkyl, or
  —C(O)R'', wherein R'' is
    $C_{1-6}$-alkyl,
    3 to 7-membered heterocycloalkyl, optionally substituted with one, two or three $C_{1-6}$-alkyl, —C(O)O—$C_{1-6}$-alkyl, or —S(O)$_2$—$C_{1-6}$-alkyl, or
    NR$^j$R$^k$, wherein R$^j$ and R$^k$ are each independently
      hydrogen,
      $C_{1-6}$-alkyl, or
      —($C_{2-6}$-alkylene)-NR$^l$R$^m$; wherein R$^l$ and R$^m$ are each independently hydrogen, $C_{1-6}$-alkyl, or —C(O)O—$C_{1-6}$-alkyl;
$R^3$, $R^4$, $R^5$, $R^6$ are each independently hydrogen, halo, $C_{1-6}$-alkyl, halo-$C_{1-6}$-alkyl, $C_{1-6}$-alkoxy or halo-$C_{1-6}$-alkoxy;
or $R^7$ and $R^6$ together with the indole ring to which they are attached form a 6 membered heterocycle which is optionally substituted with residues selected from =O, C(O)O—$C_{1-6}$-alkyl and $C_{1-6}$-alkyl;
$R^7$ is hydrogen or $C_{1-6}$-alkyl;
$R^8$ is hydrogen, halo, methyl, methoxy, $CF_3$, or $OCF_3$;
or a pharmaceutically acceptable salt thereof.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The compounds of formula (I) possess pharmaceutical activity, in particular they are modulators of V1a receptor activity. More particular, the compounds are antagonists of the V1a receptor. Such antagonists are useful as therapeutics in the conditions of dysmenorrhea, hypertension, chronic heart failure, inappropriate secretion of vasopressin, liver cirrhosis, nephrotic syndrome, obsessive compulsive disorder, anxiety and depressive disorders. The preferred indications with regard to the present invention are the treatment of anxiety and depressive disorders.

DETAILED DESCRIPTION OF THE INVENTION

Unless otherwise stated, the following terms used in the present description have the definitions given in the following. It must be noted that, as used in the specification and the appended claims, the singular forms "a", "an," and "the" include plural forms unless the context clearly dictates otherwise.

In the present description, the term "alkyl," alone or in combination with other groups, refers to a branched or straight-chain monovalent saturated hydrocarbon radical. The term "$C_{1-6}$-alkyl" denotes a saturated straight- or branched-chain hydrocarbon group containing from 1 to 6 carbon atoms, for example, methyl, ethyl, n-propyl, isopropyl, n-butyl, isobutyl, tert-butyl, the isomeric pentyls and the like. A preferred sub-group of $C_{1-6}$-alkyl is $C_{1-4}$-alkyl, i.e. with 1-4 carbon atoms.

In the present invention, the term "alkylene" refers to a linear or branched saturated divalent hydrocarbon radical. In particular, "$C_{1-6}$-alkylene", means a linear saturated divalent hydrocarbon radical of one to six carbon atoms or a branched saturated divalent hydrocarbon radical of three to six carbon atoms, e.g. methylene, ethylene, 2,2-dimethylethylene, n-propylene, 2-methylpropylene, 1-methyl-ethylene, 2-methyl-ethylene and the like.

In the present description, the terms "alkoxy" and "$C_{1-6}$-alkoxy" refer to the group R'—O—, wherein R' is alkyl or $C_{1-6}$-alkyl as defined above. Examples of alkoxy groups are methoxy, ethoxy, n-propoxy, isopropoxy, n-butoxy, tert-butoxy, sec-butoxy and the like. A preferred sub-group of $C_{1-6}$-alkoxy, and still more preferred alkoxy groups are methoxy and/or ethoxy. In the present description, the term "thioalkyl" and "$C_{1-6}$-thioalkyl" refers to the group R'—S—, wherein R' is alkyl or $C_{1-6}$-alkyl as defined above. The term "—S(O)$_{0-2}C_{1-6}$-alkyl" hence refers to the residues —S—$C_{1-16}$-alkyl, —S(O)—$C_{1-16}$-alkyl, and —S(O)$_2$—$C_{1-16}$-alkyl wherein $C_{1-6}$-alkyl is as defined above.

The term "$C_{1-6}$-alkyl substituted by OH" is synonymous with "$C_{1-6}$-hydroxyalkyl" or "hydroxyl-$C_{1-6}$-alkyl" and means a $C_{1-6}$-alkyl group as defined above wherein at least one of the hydrogen atoms of the alkyl group is replaced by a hydroxy group.

The term "$C_{1-6}$-alkyl substituted by CN" is synonymous with "$C_{1-6}$-cyanoalkyl" or "cyano-$C_{1-6}$-alkyl" and means a $C_{1-6}$-alkyl group as defined above wherein at least one of the hydrogen atoms of the alkyl group is replaced by a CN group.

The terms "halo" or "halogen" refer to fluorine (F), chlorine (Cl), bromine (Br) and iodine (I) with fluorine, chlorine and bromine being preferred.

The term "halo-$C_{1-6}$-alkyl" is synonymous with "$C_{1-6}$-haloalkyl" or "$C_{1-6}$-alkyl substituted by halo" and means a $C_{1-6}$-alkyl group as defined above wherein at least one of the hydrogen atoms of the alkyl group is replaced by a halogen atom, preferably fluoro or chloro, most preferably fluoro. Examples of halo-$C_{1-6}$-alkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Among the preferred halo-$C_{1-6}$-alkyl groups are difluoro- or trifluoro-methyl or -ethyl.

The term "halo-$C_{1-6}$-alkoxy" is synonymous with "$C_{1-6}$-haloalkoxy" or "$C_{1-6}$-alkoxy substituted by halo" and means a $C_{1-6}$-alkoxy group as defined above wherein at least one of the hydrogen atoms of the alkyl group is replaced by a halogen atom, preferably fluoro or chloro, most preferably fluoro. Among the preferred halogenated alkoxy groups are difluoro- or trifluoro-methoxy or -ethoxy.

The term "$C_{2-12}$-alkenyl," alone or in combination, denotes a straight-chain or branched hydrocarbon residue of 2 to 12 carbon atoms comprising at least one double bond. A preferred sub-group of $C_{2-12}$-alkenyl is $C_{2-6}$-alkyenyl. Examples of the preferred alkenyl groups are ethenyl, propen-1-yl, propen-2-yl (allyl), buten-1-yl, buten-2-yl, buten-3-yl, penten-1-yl, penten-2-yl, penten-3-yl, penten-4-yl, hexen-1-yl, hexen- 2-yl, hexen-3-yl, hexen-4-yl and hexen-5-yl, as well as those specifically illustrated by the examples herein below.

The term "5 or 6 membered heteroaryl" means a monovalent aromatic ring of 5 or 6 ring atoms as ring members containing one, two, three or four ring heteroatoms selected from N, O, and S, the rest being carbon atoms, whereby one, two or three heteroatoms are preferred, and one or two heteroatoms are even more preferred. Examples of heteroaryl moieties include, but are not limited to pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. 5 or 6-membered heteroaryl are optionally substituted with one or more substituents. These optional substituents include halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —S(O)$_{0-2}C_{1-6}$-alkyl, nitro, hydroxy, cyano, —($C_{1-6}$-alkylene)-O—$C_{1-6}$-alkyl, —($C_{1-6}$-alkylene)-O—$C_{1-6}$-haloalkyl, —($C_{1-6}$-alkylene)-OR''', —C(O)OC$_{1-6}$-alkyl, —C(O)C$_{1-6}$-alkyl, —C(O)OR''', —C(O)R''', —C(O)NR'R'', —S(O)$_2$NR'R'', —(CH$_2$)$_x$—NR'R'', —(CH$_2$)$_x$—NR'C(O)—$C_{1-6}$-alkyl, —(CH$_2$)$_x$—NR'S(O)$_2$—$C_{1-6}$-alkyl, —(CH$_2$)$_x$—$C_{3-6}$-cycloalkyl, —(CH$_2$)$_x$—R''', wherein x is from 0 to 4, R' and R'' are each independently H or $C_{1-6}$-alkyl, or R' and R'' together with the nitrogen to which they are bound form a 5 or 6-membered heterocycle comprising one or two heteroatoms selected from N, O and S, and R''' is phenyl or 5- to 6-membered heteroaryl, optionally substituted with one, two, or three halo, $C_{1-6}$-haloalkyl, $C_{1-6}$-alkyl, or $C_{1-6}$-alkoxy. Preferred substituents are halo, $C_{1-6}$-haloalkyl, $C_{1-6}$-alkyl, $C_{1-6}$-alkoxy, $C_{1-6}$-haloalkoxy, cyano, $C_{1-6}$-cyanoalkyl, —CH$_2$OCH$_3$, —S(O)$_2$—$C_{1-6}$-alkyl, $C_{1-6}$-hydroxyalkyl, —C(O)OC$_{1-6}$-alkyl, —NR'C(O)—$C_{1-6}$-alkyl, —NHS(O)$_2C_{1-6}$-alkyl, —C(O)N($C_{1-6}$-alkyl)$_2$, —C(O)NH($C_{1-6}$-alkyl), —S(O)$_2$N($C_{1-6}$-alkyl)$_2$, or —S(O)$_2$NH($C_{1-6}$-alkyl), or those substituents as specifically indicated herein.

The term "heterocycloalkyl" means a monovalent saturated ring, consisting of one ring of 3 to 7, preferably from 4 to 6 atoms as ring members, including one, two, three or four heteroatoms chosen from nitrogen, oxygen or sulfur, the rest being carbon atoms, whereby one, two or three heteroatoms are preferred, and one or two heteroatoms are even more preferred. It is understood that the number of heteroatoms depends on the ring size, i.e. 3 and 4-membered heterocycloalkyl preferably contain one heteroatom, 5 to 7-membered heterocycloalkyl preferably contain one, two or three heteroatoms, and even more preferably one or two heteroatoms. Examples of heterocyclic moieties include, but are not limited to, oxiranyl, thiiranyl, aziridinyl, oxetanyl, azetidinyl, tetrahydro-furanyl, tetrahydro-thiophenyl (synonymous with tetrahydro-thienyl), pyrrolidinyl, pyrazolidinyl, imidazolidinyl, oxazidinyl, isoxazidinyl, thiazolidinyl, isothiazolidinyl, piperidinyl, piperazidinyl, morpholinyl, or tetrahydropyranyl, each of which is optionally substituted as described herein. 3 to 7-membered heterocycloalkyl are optionally substituted with one or more substituents. These optional substituents include halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —S(O)$_{0-2}C_{1-6}$-alkyl, nitro, hydroxy, cyano, —($C_{1-6}$-alkylene)-O—$C_{1-6}$-alkyl, —($C_{1-6}$-alkylene)-O—$C_{1-6}$-haloalkyl, —($C_{1-6}$-alkylene)-OR''', —C(O)OC$_{1-6}$-alkyl, —C(O)C$_{1-6}$-alkyl, —C(O)OR''', —C(O)R''', —C(O)NR'R'', —S(O)$_2$NR'R'', —(CH$_2$)$_x$—NR'R'', —(CH$_2$)$_x$—NR'C(O)—$C_{1-6}$-alkyl, —(CH$_2$)$_x$—NR'S(O)$_2$—$C_{1-6}$-alkyl, —(CH$_2$)$_x$—$C_{3-6}$-cycloalkyl, —(CH$_2$)$_x$—R''', wherein x is from 0 to 4, R' and R'' are each independently H or $C_{1-6}$-alkyl, or R' and R'' together with the nitrogen to which they are bound form a 5 or 6-membered heterocycle comprising one or two heteroatoms selected from N, O and S, and R''' is phenyl or 5- to 6-membered heteroaryl, optionally substituted with one, two, or three halo, $C_{1-6}$-haloalkyl, $C_{1-6}$-alkyl, or $C_{1-6}$-alkoxy. Preferred substituents are halo, $C_{1-6}$-haloalkyl, $C_{1-6}$-alkyl, $C_{1-6}$-alkoxy, $C_{1-6}$-haloalkoxy, cyano, $C_{1-6}$-cyanoalkyl, —CH$_2$OCH$_3$, —S(O)$_2$—$C_{1-6}$-alkyl, $C_{1-6}$-hydroxyalkyl, —C(O)OC$_{1-6}$-alkyl, —NR'C(O)—$C_{1-6}$-alkyl, —C(O)N($C_{1-6}$-alkyl)$_2$, —C(O)NH($C_{1-6}$-alkyl), —NHS(O)$_2C_{1-6}$-alkyl, —S(O)$_2$N($C_{1-6}$-alkyl)$_2$, or —S(O)$_2$NH($C_{1-6}$-alkyl), or those substituents as specifically indicated herein.

The term "one or more substituents" indicates that in principle every position in the aryl (in particular phenyl), heteroaryl, heterocycloalkyl and cycloalkyl residue may bear such a substituent. The pentafluorophenyl residue may be mentioned as an example. However, in 5 to 6-membered aromatic rings, one, two, or three substituents are preferred. In 5 to 6-membered saturated rings, one, two three or four substituents are preferred. In 3 to 4-membered rings, one or two substituents are preferred.

The term "heterocycle" in the definition "R' and R'', together with the nitrogen to which they are bound form a five- or six-membered heterocycle comprising one or two heteroatoms selected from the group of nitrogen, oxygen and sulfur" means either heterocycloalkyl or partially unsaturated heterocycloalkyl (synonymous with heterocycloalkenyl), which may optionally be substituted with one, two or three substituents selected from halo, $C_{1-6}$-haloalkyl, $C_{1-6}$-alkyl, $C_{1-6}$-alkoxy, $C_{1-6}$-haloalkoxy, nitro, and cyano. Preferred heterocycles are piperazine, N-methylpiperazine, morpholin, piperidine and pyrrolidine.

Examples of group illustrating the expression "$R^1$ and $R^6$ together with the indole ring to which they are attached form a 6 membered heterocycle which is optionally substituted by =O, C(O)O—$C_{1-6}$-alkyl or $C_{1-6}$-alkyl" preferably are:

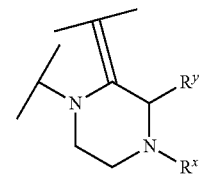

wherein $R^x$ is hydrogen, $C_{1-6}$-alkyl, C(O)O—$C_{1-6}$-alkyl, and $R^y$ is hydrogen or =O.

The term "$C_{3-7}$-cycloalkyl" denotes a monovalent or divalent saturated carbocyclic moiety consisting of a monocyclic ring containing from 3 to 7 ring carbon atoms. Cycloalkyl can optionally be substituted with one, two, three or four substituents, wherein each substituent is independently hydroxy, $C_{1-6}$-alkyl, $C_{1-6}$-alkoxy, halogen, amino, unless otherwise specifically indicated. Examples of cycloalkyl moieties include optionally substituted cyclopropyl, optionally substituted cyclobutyl, optionally substituted cyclopentyl and optionally substituted cyclohexyl as well as those specifically illustrated by the examples herein below.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salt" or "pharmaceutically acceptable salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The invention further comprises individual optical isomers of the compounds herein as well as racemic and non-racemic mixtures thereof.

In detail, the present invention relates to compounds of the general formula (I)

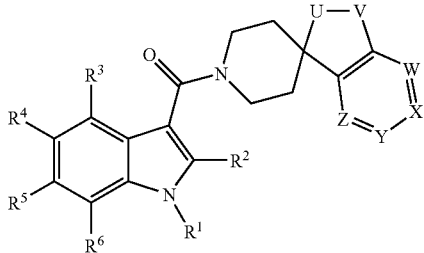

wherein
U is O, and V is $CH_2$,
U is O, and V is C=O,
U is $CH_2$, and V is O,
U—V is —CH=CH—,
U—V is —$CH_2$—$CH_2$—,
U is $CH_2$, V is $NR^7$;
U is C=O, and V is $NR^7$, or
U is C=O and V is O;
one or two of the variables W, X, Y and Z are nitrogen, the remaining variables being $CR^8$;
$R^1$ is H,
 $C_{1-12}$-alkyl, optionally substituted with CN or OH,
 $C_{1-6}$-haloalkyl,
 $C_{2-12}$-alkenyl,
 —$(CR^iR^{ii})_m$—$R^a$,
  wherein $R^i$ and $R^{ii}$ are independently from each other H, methyl, or ethyl;
  wherein m is from 0 to 4;
  wherein $R^a$ is
   phenyl, 5- to 6-membered heteroaryl, 3- to 7-membered heterocycloalkyl or 3 to 7-membered cyloalkyl, or
   which are optionally substituted with one or more A,
   —$NR^bR^c$, wherein $R^b$ and $R^c$ are each independently
    hydrogen,
    hydroxy,
    $C_{1-6}$-alkyl,
    —$S(O)_2$—$C_{1-6}$-alkyl, or
    —C(O)—$C_{1-6}$-alkyl,
 —$(CR^{iii}R^{iv})_n$—$C(O)R^d$,
  wherein $R^{iii}$ and $R^{iv}$ are independently from each other H, methyl, or ethyl;
  wherein n is from 0 to 4;
  wherein $R^d$ is
   $C_{1-6}$-alkoxy,
   —$NR^eR^f$, wherein $R^e$ and $R^f$ are each independently
    hydrogen,
    $C_{1-6}$-alkyl, or
    —$(C_{2-6}$-alkylene)-$NR^gR^h$; wherein $R^g$ and $R^h$ are each independently hydrogen, $C_{1-6}$-alkyl, or
    —C(O)O—$C_{1-6}$-alkyl, or phenyl, 5- to 6-membered heteroaryl, 3- to 7-membered heterocycloalkyl or 3 to 7-membered cyloalkyl,
 which are optionally substituted with one or more A,
—$S(O)_2$-phenyl, wherein phenyl is optionally substituted with one or more halo, $C_{1-6}$-haloalkyl, $C_{1-6}$-alkyl, $C_{1-6}$-alkoxy, $C_{1-6}$-haloalkoxy, nitro, hydroxy or cyano;
—$S(O)_2$—$C_{1-6}$-alkyl,
—$S(O)_2N(C_{1-6}$-alkyl$)_2$, or
—$S(O)_2NH(C_{1-6}$-alkyl);
A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy,
 —$S(O)_{0-2}C_{1-6}$-alkyl, nitro, hydroxy, cyano, —$(C_{1-6}$-alkylene)-O—$C_{1-6}$-alkyl, —$(C_{1-6}$-alkylene)-O—$C_{1-6}$-haloalkyl, —$(C_{1-6}$-alkylene)-OR''', —C(O)O$C_{1-6}$-alkyl, —C(O)$C_{1-6}$-alkyl, —C(O)OR''', —C(O)R''', —C(O)NR'R'', —$S(O)_2NR'R''$, —$(CH_2)$, —NR'R'', —$(CH_2)$, —NR'C(O)—$C_{1-6}$-alkyl, —$(CH_2)$, —NR'S(O)_2—$C_{1-6}$-alkyl, —$(CH_2)$, —$C_{3-6}$-cycloalkyl, or —$(CH_2)_x$—R''',
 wherein x is from 0 to 4,
 R' and R'' are each independently H or $C_{1-6}$-alkyl, or
 R' and R'' together with the nitrogen to which they are bound form a 5 or 6-membered heterocycle comprising one or two heteroatoms selected from N, O and S, and
 R''' is phenyl or 5- to 6-membered heteroaryl, optionally substituted with one, two, or three halo, $C_{1-6}$-haloalkyl, $C_{1-6}$-alkyl, or $C_{1-6}$-alkoxy,
$R^2$ is hydrogen,
 $C_{1-6}$-alkyl, or
 —C(O)R'', wherein R'' is
  $C_{1-6}$-alkyl,
  3 to 7-membered heterocycloalkyl, optionally substituted with one, two or three $C_{1-6}$-alkyl, —C(O)O—$C_{1-6}$-alkyl, or —$S(O)_2$—$C_{1-6}$-alkyl, or
  $NR^jR^k$, wherein $R^j$ and $R^k$ are each independently
   hydrogen,
   $C_{1-6}$-alkyl, or
   —$(C_{2-6}$-alkylene)-$NR^lR^m$; wherein $R^l$ and $R^m$ are each independently hydrogen, $C_{1-6}$-alkyl, or —C(O)O—$C_{1-6}$-alkyl;
$R^3$, $R^4$, $R^5$, $R^6$ are each independently hydrogen, halo, $C_{1-6}$-alkyl, halo-$C_{1-6}$-alkyl, $C_{1-6}$-alkoxy or halo-$C_{1-6}$-alkoxy;
or $R^1$ and $R^6$ together with the indole ring to which they are attached form a 6 membered heterocycle which is optionally substituted with residues selected from =O, C(O)O—$C_{1-6}$-alkyl and $C_{1-6}$-alkyl;
$R^7$ is hydrogen or $C_{1-6}$-alkyl;
$R^8$ is hydrogen, halo, methyl, methoxy, $CF_3$, or $OCF_3$;
or a pharmaceutically acceptable salt thereof.

In the following, certain embodiments of the invention are disclosed, whereby the combination of each of these embodiments with each other embodiment is also encompassed by present invention.

In certain embodiments of the invention, $R^1$ is hydrogen. However, it is preferred that not all residues $R^1$ to $R^6$ are simultaneously hydrogen.

In certain embodiments of the invention, $R^1$ is $C_{1-12}$-alkyl, optionally substituted with CN or OH; or $R^1$ is $C_{2-12}$-alkyl, optionally substituted with CN or OH. Preferably, $R^1$ is $C_{1-6}$-alkyl, optionally substituted with CN or OH; or $R^1$ is $C_{2-6}$-alkyl, optionally substituted with CN or OH.

In certain embodiments of the invention, $R^1$ is $C_{1-6}$-haloalkyl or $C_{2-12}$-alkenyl. In case $R^1$ is alkenyl, $C_{2-6}$-alkenyl is preferred.

In certain embodiments of the invention,
$R^1$ is $(CR^iR^{ii})_m$—$R^a$,
wherein $R^i$ and $R^{ii}$ are independently from each other H, methyl, or ethyl;
wherein m is from 0 to 4;
wherein $R^a$ is
phenyl, 5- to 6-membered heteroaryl, 3- to 7-membered heterocycloalkyl or 3 to 7-membered cyloalkyl,
which are optionally substituted with one or more halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —$S(O)_{0-2}C_{1-6}$-alkyl, nitro, hydroxy, cyano, —$(C_{1-6}$-alkylene)-O—$C_{1-6}$-alkyl, —$(C_{1-6}$-alkylene)-O—$C_{1-6}$-haloalkyl, —$(C_{1-6}$-alkylene)-OR''', —C(O)O$C_{1-6}$-alkyl, —C(O)$C_{1-6}$-alkyl, —C(O)OR''', —C(O)R''', —C(O)NR'R'', —$S(O)_2$NR'R'', —$(CH_2)_x$—NR'R'', —$(CH_2)_x$—NR'C(O)—$C_{1-6}$-alkyl, —$(CH_2)_x$—NR'S(O)$_2$—$C_{1-6}$-alkyl, —$(CH_2)_x$—$C_{3-6}$-cycloalkyl, or —$(CH_2)_x$—R''',
wherein x is from 0 to 4,
R' and R'' are each independently H or $C_{1-6}$-alkyl, or
R' and R'' together with the nitrogen to which they are bound form a 5 or 6-membered heterocycle comprising one or two heteroatoms selected from N, O and S, and
R''' is phenyl or 5- to 6-membered heteroaryl, optionally substituted with one, two, or three halo, $C_{1-6}$-haloalkyl, $C_{1-6}$-alkyl, or $C_{1-6}$-alkoxy, or
—NR$^b$R$^c$, wherein R$^b$ and R$^c$ are each independently
hydrogen,
hydroxy,
$C_{1-6}$-alkyl,
—$S(O)_2$—$C_{1-6}$-alkyl, or
—C(O)—$C_{1-6}$-alkyl.

In —$(CR^iR^{ii})_m$—$R^a$, preferably, all $R^i$ and $R^{ii}$ are hydrogen, or one $R^i$ is methyl and the other $R^i$ and $R^{ii}$ are hydrogen. The following linkers —$(CR^iR^{ii})_m$— are preferred: —$CH_2$—, —$CH(CH_3)$—, —$CH_2CH_2$—, —$CH_2CH_2CH_2$—, —$CH(CH_3)CH_2$—, —$CH_2CH(CH_3)$—, —$CH(CH_3)CH_2CH_2$—, —$CH_2CH(CH_3)CH_2$—, or —$CH_2CH_2CH(CH_3)$—.

The variable m in —$(CR^iR^{ii})_m$—$R^a$ is 0, 1, 2, 3 or 4. In case $R^a$ is —NR$^b$R$^c$, m is preferably 1, 2, 3 or 4.

When $R^a$ in —$(CR^iR^{ii})_m$—$R^a$ is 5 to 6-membered heteroaryl, then 5- to 6-membered heteroaryl is as defined above, namely pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. In case m is 0, pyridinyl is preferred, in case m is 1, 2, 3 or 4, pyridinyl, pyrimidinyl, pyrazinyl, pyridazinyl, imidazolyl, pyrazolyl, oxazolyl, isoxazolyl, or thiazolyl are preferred. All these residues are optionally substituted as described herein.

When $R^a$ in —$(CR^iR^{ii})_m$—$R^a$ is a 3- to 7-membered heterocycloalkyl, then 3- to 7-membered heterocycloalkyl is as defined above, namely oxiranyl, thiiranyl, aziridinyl, oxetanyl, azetidinyl, tetrahydro-furanyl, tetrahydro-thiophenyl (synonymous with tetrahydro-thienyl), pyrrolidinyl, pyrazolidinyl, imidazolidinyl, oxazidinyl, isoxazidinyl, thiazolidinyl, isothiazolidinyl, piperidinyl, piperazidinyl, morpholinyl, or tetrahydropyranyl. When $R^a$ is 3- to 7-membered heterocycloalkyl, oxiranyl, oxetanyl, pyrrolidinyl, piperidinyl, piperazidinyl, morpholinyl, or tetrahydropyranyl are preferred. All these residues are optionally substituted as described herein.

When R''' is 5 to 6-membered heteroaryl, then 5- to 6-membered heteroaryl is as defined above, namely pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. Pyridinyl, pyrimidinyl, imidazolyl, pyrazolyl, oxazolyl, isoxazolyl, or thiazolyl are preferred.

In certain embodiments of the invention,
$R^1$ is —$(CR^{iii}R^{iv})_n$—C(O)$R^d$,
wherein $R^{iii}$ and $R^{iv}$ are independently from each other H, methyl, or ethyl;
wherein n is from 0 to 4;
wherein $R^d$ is
$C_{1-6}$-alkoxy,
—NR$^e$R$^f$, wherein R$^e$ and R$^f$ are each independently
hydrogen,
$C_{1-6}$-alkyl, or
—$(C_{2-6}$-alkylene)-NR$^g$R$^h$; wherein R$^g$ and R$^h$ are each independently hydrogen, $C_{1-6}$-alkyl, or —C(O)O—$C_{1-6}$-alkyl, or
phenyl, 5- to 6-membered heteroaryl, 3- to 7-membered heterocycloalkyl or 3 to 7-membered cyloalkyl,
which are optionally substituted with one or more halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —$S(O)_{0-2}C_{1-16}$-alkyl, nitro, hydroxy, cyano, —$(C_{1-6}$-alkylene)-O—$C_{1-6}$-alkyl, —$(C_{1-6}$-alkylene)-O—$C_{1-6}$-haloalkyl, —$(C_{1-6}$-alkylene)-OR''', —C(O)O$C_{1-6}$-alkyl, —C(O)$C_{1-6}$-alkyl, —C(O)OR''', —C(O)R''', —C(O)NR'R'', —$S(O)_2$NR'R'', —$(CH_2)_x$—NR'R'', —$(CH_2)_x$—NR'C(O)—$C_{1-6}$-alkyl, —$(CH_2)_x$—NR'S(O)$_2$—$C_{1-6}$-alkyl, —$(CH_2)_x$—$C_{3-6}$-cycloalkyl, or —$(CH_2)_x$—R''',
wherein x is from 0 to 4,
R' and R'' are each independently H or $C_{1-6}$-alkyl, or
R' and R'' together with the nitrogen to which they are bound form a 5 or 6-membered heterocycle comprising one or two heteroatoms selected from N, O and S, and
R''' is phenyl or 5- to 6-membered heteroaryl, optionally substituted with one, two, or three halo, $C_{1-6}$-haloalkyl, $C_{1-6}$-alkyl, or $C_{1-6}$-alkoxy.

In —$(CR^{iii}R^{iv})_n$—C(O)$R^d$, preferably, all $R^{iii}$ and $R^{iv}$ are hydrogen, or one $R^{iii}$ is methyl and the other $R^{iii}$ and $R^{iv}$ are hydrogen. The following linkers —$(CR^iR^{ii})_n$— are preferred: —$CH_2$—, —$CH(CH_3)$—, —$CH_2CH_2$—, —$CH_2CH_2CH_2$—, —$CH(CH_3)CH_2$—, —$CH_2CH(CH_3)$—, —$CH(CH_3)CH_2CH_2$—, —$CH_2CH(CH_3)CH_2$—, or —$CH_2CH_2CH(CH_3)$—.

The variable n in —$(CR^{iii}R^{iv})_n$—C(O)$R^d$ is 0, 1, 2, 3 or 4.

When $R^d$ in —$(CR^{iii}R^{iv})_n$—C(O)$R^d$ is 5 to 6-membered heteroaryl, then 5- to 6-membered heteroaryl is as defined above, namely pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. When $R^d$ is 5- to 6-membered heteroaryl, optionally substituted pyridinyl is preferred. All these residues are optionally substituted as described herein.

When $R^d$ in —$(CR^{iii}R^{iv})_n$—C(O)$R^d$ is a 3- to 7-membered heterocycloalkyl, then 3- to 7-membered heterocycloalkyl is as defined above, namely oxiranyl, thiiranyl, aziridinyl, oxetanyl, azetidinyl, tetrahydro-furanyl, tetrahydro-thiophenyl (synonymous with tetrahydro-thienyl), pyrrolidinyl, pyrazolidinyl, imidazolidinyl, oxazidinyl, isoxazidinyl, thiazolidinyl, isothiazolidinyl, piperidinyl, piperazinyl, morpholinyl, or tetrahydropyranyl. When $R^d$ is 3- to 7-membered heterocycloalkyl, optionally substituted piperidinyl, piperazidinyl, or morpholinyl are preferred. All these residues are optionally substituted as described herein.

When R''' is 5 to 6-membered heteroaryl, then 5- to 6-membered heteroaryl is as defined above, namely pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl. Pyridinyl, pyrimidinyl, imidazolyl, pyrazolyl, oxazolyl, isoxazolyl, or thiazolyl are preferred.

In certain embodiments of the invention, $R^1$ is —S(O)$_2$-phenyl, wherein phenyl is optionally substituted with one or more halo, $C_{1-6}$-haloalkyl, $C_{1-6}$-alkyl, $C_{1-6}$-alkoxy, $C_{1-6}$-haloalkoxy, nitro, hydroxy or cyano. Halo, $CF_3$, $C_{1-4}$-alkyl, $C_{1-6}$-alkoxy, $OCF_3$ and cyano are preferred substituents.

In certain embodiments of the invention, $R^1$ is —S(O)$_2$—$C_{1-16}$-alkyl, —S(O)$_2$N($C_{1-6}$-alkyl)$_2$, or —S(O)$_2$NH($C_{1-6}$-alkyl).

It is understood that all the above residues $R^1$ are encompassed by present invention in all their possible combinations. Some examples are given below.

In certain embodiments of the invention,
A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —S(O)$_{0-2}C_{1-16}$-alkyl, nitro, cyano, —($C_{1-6}$-alkylene)-O—$C_{1-6}$-alkyl, —($C_{1-6}$-alkylene)-OR''', —C(O)O$C_{1-6}$-alkyl, —C(O)NR'R'', —S(O)$_2$NR'R'', —(CH$_2$)$_x$—NR'R'', —(CH$_2$)$_x$—NR'C(O)—$C_{1-6}$-alkyl, —(CH$_2$)$_x$—NR'S(O)$_2$—$C_{1-6}$-alkyl, —(CH$_2$)$_x$—$C_{3-6}$-cycloalkyl, or —(CH$_2$)$_x$—R''',
wherein x is from 0 to 4,
R' and R'' are each independently H or $C_{1-6}$-alkyl, or
R' and R'' together with the nitrogen to which they are bound form a 5 or 6-membered heterocycle comprising one or two heteroatoms selected from N, O and S, and
R''' is phenyl, optionally substituted with one, two, or three halo, $C_{1-6}$-haloalkyl, $C_{1-6}$-alkyl, or $C_{1-6}$-alkoxy.

In certain embodiments of formula (I) of the invention,
A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, $C_{1-6}$-thioalkyl, —S(O)$_2$—$C_{1-6}$-alkyl, cyano, —CH$_2$OCH$_3$, —C(O)O—$C_{1-6}$-alkyl, —C(O)NR'R'', —S(O)$_2$NR'R'', —NR'C(O)—$C_{1-6}$-alkyl, —NR'S(O)$_2$—$C_{1-6}$-alkyl, benzyl, or phenyl
wherein R' and R'' are each independently H or $C_{1-6}$-alkyl.

In certain embodiments of formula (I) of the invention,
$R^1$ is H,
$C_{2-6}$-alkyl, optionally substituted with CN or OH,
$C_{1-6}$-haloalkyl,
—(CR$^i$R$^{ii}$)$_m$—R$^a$,
wherein R$^i$ and R$^{ii}$ are independently from each other H, methyl, or ethyl;
wherein m is from 0 to 4;
wherein R$^a$ is
phenyl, 5- to 6-membered heteroaryl, 3- to 7-membered heterocycloalkyl or 3 to 7-membered cyloalkyl,
which are optionally substituted with one or more A, or
—NR$^b$R$^c$, wherein R$^b$ and R$^c$ are each independently hydrogen, $C_{1-6}$-alkyl, —S(O)$_2$—$C_{1-6}$-alkyl, or —C(O)—$C_{1-6}$-alkyl,
—(CR$^{iii}$R$^{iv}$)$_n$—C(O)R$^d$,
wherein R$^{iii}$ and R$^{iv}$ are independently from each other H, methyl, or ethyl;
wherein n is from 0 to 4;
wherein R$^d$ is
$C_{1-6}$-alkoxy,
—NR$^e$R$^f$, wherein R$^e$ and R$^f$ are each independently hydrogen,
$C_{1-6}$-alkyl, or
—($C_{2-6}$-alkylene)-NR$^g$R$^h$; wherein R$^g$ and R$^h$ are each independently hydrogen, $C_{1-6}$-alkyl, or —C(O)O—$C_{1-6}$-alkyl, or
phenyl, 5- to 6-membered heteroaryl, 3- to 7-membered heterocycloalkyl or 3 to 7-membered cyloalkyl,
which are optionally substituted with one or more A,
—S(O)$_2$—$C_{1-6}$-alkyl,
—S(O)$_2$N($C_{1-6}$-alkyl)$_2$, or
—S(O)$_2$NH($C_{1-6}$-alkyl);
A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —S(O)$_{0-2}C_{1-6}$-alkyl, nitro, hydroxy, cyano, —($C_{1-6}$-alkylene)-O—$C_{1-6}$-alkyl, —($C_{1-6}$-alkylene)-O—$C_{1-6}$-haloalkyl, —($C_{1-6}$-alkylene)-OR''', —C(O)O$C_{1-6}$-alkyl, —C(O)$C_{1-6}$-alkyl, —C(O)OR''', —C(O)R''', —C(O)NR'R'', —S(O)$_2$NR'R'', —(CH$_2$), —NR'R'', —(CH$_2$), —NR'C(O)—$C_{1-6}$-alkyl, —(CH$_2$), —NR'S(O)$_2$—$C_{1-6}$-alkyl, —(CH$_2$), —$C_{3-6}$-cycloalkyl, or —(CH$_2$)$_x$—R''',
wherein x is from 0 to 4,
R' and R'' are each independently H or $C_{1-6}$-alkyl, or
R' and R'' together with the nitrogen to which they are bound form a 5 or 6-membered heterocycle comprising one or two heteroatoms selected from N, O and S, and
R''' is phenyl or 5- to 6-membered heteroaryl, optionally substituted with one, two, or three halo, $C_{1-6}$-haloalkyl, $C_{1-6}$-alkyl, or $C_{1-6}$-alkoxy.

In certain embodiments of formula (I) of the invention,
$R^1$ is H,
$C_{2-6}$-alkyl, optionally substituted with CN or OH,
$C_{1-6}$-haloalkyl,
—(CR$^i$R$^{ii}$)$_m$—R$^a$,
wherein R$^i$ and R$^{ii}$ are independently from each other H, methyl, or ethyl;
wherein m is from 1 to 4;
wherein R$^a$ is
phenyl, 5- to 6-membered heteroaryl, 3- to 7-membered heterocycloalkyl or 3 to 7-membered cyloalkyl,
which are optionally substituted with one or more A, or
—NR$^b$R$^c$, wherein R$^b$ and R$^c$ are each independently hydrogen, $C_{1-6}$-alkyl, —S(O)$_2$—$C_{1-6}$-alkyl, or —C(O)—$C_{1-6}$-alkyl,
—(CR$^{iii}$R$^{iv}$)$_n$—C(O)R$^d$,
wherein R$^{iii}$ and R$^{iv}$ are independently from each other H, methyl, or ethyl;
wherein n is from 0 to 4;
wherein R$^d$ is
$C_{1-6}$-alkoxy,
—NR$^e$R$^f$, wherein R$^e$ and R$^f$ are each independently hydrogen,
$C_{1-6}$-alkyl, or
—($C_{2-6}$-alkylene)-NR$^g$R$^h$; wherein R$^g$ and R$^h$ are each independently hydrogen, $C_{1-6}$-alkyl, or —C(O)O—$C_{1-6}$-alkyl, or phenyl, 5- to 6-membered heteroaryl, 3- to 7-membered heterocycloalkyl or 3 to 7-membered cyloalkyl,
which are optionally substituted with one or more A,
—S(O)$_2$—C$_{1-6}$-alkyl,
—S(O)$_2$N(C$_{1-6}$-alkyl)$_2$, or
—S(O)$_2$NH(C$_{1-6}$-alkyl);

A is halo, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, —S(O)$_{0-2}$C$_{1-6}$-alkyl, nitro, cyano, —(C$_{1-6}$-alkylene)-O—C$_{1-6}$-alkyl, —(C$_{1-6}$-alkylene)-OR''', —C(O)OC$_{1-6}$-alkyl, —C(O)NR'R'', —S(O)$_2$NR'R'', —(CH$_2$)$_x$—NR'R'', —(CH$_2$)$_x$—NR'C(O)—C$_{1-6}$-alkyl, —(CH$_2$)$_x$—NR'S(O)$_2$—C$_{1-6}$-alkyl, —(CH$_2$)$_x$—C$_{3-6}$-cycloalkyl, or —(CH$_2$)$_x$—R''',
wherein x is from 0 to 4,
R' and R'' are each independently H or C$_{1-6}$-alkyl, or
R' and R'' together with the nitrogen to which they are bound form a 5 or 6-membered heterocycle comprising one or two heteroatoms selected from N, O and S, and
R''' is phenyl, optionally substituted with one, two, or three halo, C$_{1-6}$-haloalkyl, C$_{1-6}$-alkyl, or C$_{1-6}$-alkoxy.

Preferably, A is selected from
halo, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, C$_{1-6}$-thioalkyl, —S(O)$_2$—C$_{1-6}$-alkyl, cyano, —CH$_2$OCH$_3$, —C(O)O—C$_{1-6}$-alkyl, —C(O)NR'R'', —S(O)$_2$NR'R'', —NR'C(O)—C$_{1-6}$-alkyl, —NR'S(O)$_2$—C$_{1-6}$-alkyl, benzyl, and phenyl wherein R' and R'' are each independently H or C$_{1-6}$-alkyl.

When R'' in —C(O)R'' of R$^2$ is a 3- to 7-membered heterocycloalkyl, then 3- to 7-membered heterocycloalkyl is as defined above, namely oxiranyl, thiiranyl, aziridinyl, oxetanyl, azetidinyl, tetrahydro-furanyl, tetrahydro-thiophenyl (synonymous with tetrahydro-thienyl), pyrrolidinyl, pyrazolidinyl, imidazolidinyl, oxazidinyl, isoxazidinyl, thiazolidinyl, isothiazolidinyl, piperidinyl, piperazidinyl, morpholinyl, or tetrahydropyranyl. When R'' is 3- to 7-membered heterocycloalkyl, piperidinyl, piperazidinyl, or morpholinyl, optionally substituted with one methyl, are preferred.

In certain embodiments of the invention, R$^2$ of the compounds of formula (I) is hydrogen or C$_{1-6}$-alkyl.

In certain embodiments of the invention, R$^3$, R$^4$, R$^5$, R$^6$ are each independently hydrogen, halo, C$_{1-6}$-alkyl, C$_{1-6}$-haloalkyl, C$_{1-6}$-alkoxy or C$_{1-6}$-haloalkoxy.

In certain embodiments of the invention, R$^3$ and R$^6$ of formula (I) are hydrogen.

In certain embodiments of the invention, R$^4$ of formula (I) is hydrogen, Cl, F or methyl.

In certain embodiments of the invention, R$^5$ of formula (I) is hydrogen, halo, CF$_3$, methoxy or —OCF$_3$. If R$^5$ is hydrogen, R$^1$ is preferably as defined above, however, with the exclusion of hydrogen. In further embodiments, R$^5$ is halo, CF$_3$, methoxy or —OCF$_3$. In further embodiments, R$^5$ is Cl, F or methoxy; in further embodiments, R$^5$ is Cl.

In certain embodiments of the invention, R$^3$ and R$^6$ are hydrogen, R$^4$ is hydrogen, F, Cl or methyl, and R$^5$ is halo, CF$_3$, methoxy or OCF$_3$.

In preferred embodiments of the invention, not all R$^1$ to R$^6$ are hydrogen at the same time.

In certain embodiments of the invention, R$^7$ is hydrogen or C$_{1-6}$-alkyl; preferably hydrogen.

In certain embodiments of the invention, R$^8$ is hydrogen, halo, methyl, methoxy, CF$_3$, or OCF$_3$; preferably, R$^8$ is hydrogen.

In a certain embodiment the compounds of the invention are those compounds of formula (I-a), namely wherein
U is O, and V is CH$_2$; and one or two of the variables W, X, Y, and Z are nitrogen, the remaining variables being CR$^8$, wherein R$^1$ to R$^6$ and R$^8$ are as defined in any of the combinations given above.

In a certain embodiment the compounds of the invention are those compounds of formula (I-a) wherein
U is O, and V is CH$_2$; and one of the variables W, X, Y, and Z is nitrogen, the remaining variables being CR$^8$, wherein R$^1$ to R$^6$ and R$^8$ are as defined in any of the combinations given above.

In a certain embodiment the compounds of the invention are those compounds of formula (I-a) wherein
U is O, V is CH$_2$, W is N, X is CH, Y is CH, and Z is CH, or
U is O, V is CH$_2$, W is CH, X is N, Y is CH, and Z is CH, or
U is O, V is CH$_2$, W is CH, X is CH, Y is N, and Z is CH, or
U is O, V is CH$_2$, W is CH, X is CH, Y is CH, and Z is N, or
U is O, V is CH$_2$, W is N, X is CH, Y is N, and Z is CH, or
U is O, V is CH$_2$, W is N, X is CH, Y is CH, and Z is N, or
U is O, V is CH$_2$, W is CH, X is N, Y is N, and Z is CH, or
U is O, V is CH$_2$, W is CH, X is N, Y is CH, and Z is N; and
wherein R$^1$ to R$^6$ are as defined in any of the combinations given above.

Preferred embodiments of the invention are those compounds of formula (I-a) wherein
U is O, V is CH$_2$, W is N, X is CH, Y is CH, and Z is CH, or
U is O, V is CH$_2$, W is CH, X is N, Y is CH, and Z is CH, or
U is O, V is CH$_2$, W is CH, X is CH, Y is N, and Z is CH, or
U is O, V is CH$_2$, W is CH, X is CH, Y is CH, and Z is N; and
wherein R$^1$ to R$^6$ are as defined in any of the combinations given above.

In a certain embodiment the compounds of the invention are those compounds of formula (I-b), namely wherein
U is O, and V is C═O; and one or two of the variables W, X, Y, and Z are nitrogen, the remaining variables being CR$^8$, wherein R$^1$ to R$^6$ and R$^8$ are as defined in any of the combinations given above.

In a certain embodiment the compounds of the invention are those compounds of formula (I-b) wherein
U is O, and V is C═O; and one of the variables W, X, Y, and Z is nitrogen, the remaining variables being CR$^8$, wherein R$^1$ to R$^6$ and R$^8$ are as defined in any of the combinations given above.

In a certain embodiment the compounds of the invention are those compounds of formula (I-b) wherein
U is O, V is C═O, W is N, X is CH, Y is CH, and Z is CH, or
U is O, V is C═O, W is CH, X is N, Y is CH, and Z is CH, or
U is O, V is C═O, W is CH, X is CH, Y is N, and Z is CH, or
U is O, V is C═O, W is CH, X is CH, Y is CH, and Z is N, or
U is O, V is C═O, W is N, X is CH, Y is N, and Z is CH, or
U is O, V is C═O, W is N, X is CH, Y is CH, and Z is N, or
U is O, V is C═O, W is CH, X is N, Y is N, and Z is CH, or
U is O, V is C═O, W is CH, X is N, Y is CH, and Z is N; and
wherein R$^1$ to R$^6$ are as defined in any of the combinations given above.

In a certain embodiment the compounds of the invention are those compounds of formula (I-c), namely wherein
U is CH$_2$, and V is O; and one or two of the variables W, X, Y, and Z are nitrogen, the remaining variables being CR$^8$, wherein R$^1$ to R$^6$ and R$^8$ are as defined in any of the combinations given above.

In a certain embodiment the compounds of the invention are those compounds of formula (I-c) wherein U is $CH_2$, and V is O; and one of the variables W, X, Y, and Z is nitrogen, the remaining variables being $CR^8$, wherein $R^1$ to $R^6$ and $R^8$ are as defined in any of the combinations given above.

In a certain embodiment the compounds of the invention are those compounds of formula (I-c) wherein
U is $CH_2$, V is O, W is N, X is CH, Y is CH, and Z is CH, or
U is $CH_2$, V is O, W is CH, X is N, Y is CH, and Z is CH, or
U is $CH_2$, V is O, W is CH, X is CH, Y is N, and Z is CH, or
U is $CH_2$, V is O, W is CH, X is CH, Y is CH, and Z is N, or
U is $CH_2$, V is O, W is N, X is CH, Y is N, and Z is CH, or
U is $CH_2$, V is O, W is N, X is CH, Y is CH, and Z is N, or
U is $CH_2$, V is O, W is CH, X is N, Y is N, and Z is CH, or
U is $CH_2$, V is O, W is CH, X is N, Y is CH, and Z is N; and
wherein $R^1$ to $R^6$ are as defined in any of the combinations given above.

In a certain embodiment the compounds of the invention are those compounds of formula (I-d), namely wherein U—V is —CH=CH—; and one or two of the variables W, X, Y, and Z are nitrogen, the remaining variables being $CR^8$, wherein $R^1$ to $R^6$ and $R^8$ are as defined in any of the combinations given above.

In a certain embodiment the compounds of the invention are those compounds of formula (I-d) wherein U—V is —CH=CH—; and one of the variables W, X, Y, and Z is nitrogen, the remaining variables being $CR^8$, wherein $R^1$ to $R^6$ and $R^8$ are as defined in any of the combinations given above.

In a certain embodiment the compounds of the invention are those compounds of formula (I-d) wherein
U—V is —CH=CH—, W is N, X is CH, Y is CH, and Z is CH, or
U—V is —CH=CH—, W is CH, X is N, Y is CH, and Z is CH, or
U—V is —CH=CH—, W is CH, X is CH, Y is N, and Z is CH, or
U—V is —CH=CH—, W is CH, X is CH, Y is CH, and Z is N, or
U—V is —CH=CH—, W is N, X is CH, Y is N, and Z is CH, or
U—V is —CH=CH—, W is N, X is CH, Y is CH, and Z is N, or
U—V is —CH=CH—, W is CH, X is N, Y is N, and Z is CH, or
U—V is —CH=CH—, W is CH, X is N, Y is CH, and Z is N; and
wherein $R^1$ to $R^6$ are as defined in any of the combinations given above.

In a certain embodiment the compounds of the invention are those compounds of formula (I-e), namely wherein U—V is —$CH_2$—$CH_2$—; and one or two of the variables W, X, Y, and Z are nitrogen, the remaining variables being $CR^8$, wherein $R^1$ to $R^6$ and $R^8$ are as defined in any of the combinations given above.

In a certain embodiment the compounds of the invention are those compounds of formula (I-e) wherein U—V is —$CH_2$—$CH_2$—; and one of the variables W, X, Y, and Z is nitrogen, the remaining variables being $CR^8$, wherein $R^1$ to $R^6$ and $R^8$ are as defined in any of the combinations given above.

In a certain embodiment the compounds of the invention are those compounds of formula (I-e) wherein
U—V is —$CH_2$—$CH_2$—, W is N, X is CH, Y is CH, and Z is CH, or
U—V is —$CH_2$—$CH_2$—, W is CH, X is N, Y is CH, and Z is CH, or
U—V is —$CH_2$—$CH_2$—, W is CH, X is CH, Y is N, and Z is CH, or
U—V is —$CH_2$—$CH_2$—, W is CH, X is CH, Y is CH, and Z is N, or
U—V is —$CH_2$—$CH_2$—, W is N, X is CH, Y is N, and Z is CH, or
U—V is —$CH_2$—$CH_2$—, W is N, X is CH, Y is CH, and Z is N, or
U—V is —$CH_2$—$CH_2$—, W is CH, X is N, Y is N, and Z is CH, or
U—V is —$CH_2$—$CH_2$—, W is CH, X is N, Y is CH, and Z is N; and
wherein $R^1$ to $R^6$ are as defined in any of the combinations given above.

In a certain embodiment the compounds of the invention are those compounds of formula (I-f), namely wherein U is $CH_2$, V is $NR^7$; and one or two of the variables W, X, Y, and Z are nitrogen, the remaining variables being $CR^8$, wherein $R^1$ to $R^8$ are as defined in any of the combinations given above.

In a certain embodiment the compounds of the invention are those compounds of formula (I-f) wherein U is $CH_2$, V is $NR^7$; and one of the variables W, X, Y, and Z is nitrogen, the remaining variables being $CR^8$, wherein $R^1$ to $R^8$ are as defined in any of the combinations given above.

In a certain embodiment the compounds of the invention are those compounds of formula (I-f) wherein
U is $CH_2$, V is $NR^7$, W is N, X is CH, Y is CH, and Z is CH, or
U is $CH_2$, V is $NR^7$, W is CH, X is N, Y is CH, and Z is CH, or
U is $CH_2$, V is $NR^7$, W is CH, X is CH, Y is N, and Z is CH, or
U is $CH_2$, V is $NR^7$, W is CH, X is CH, Y is CH, and Z is N, or
U is $CH_2$, V is $NR^7$, W is N, X is CH, Y is N, and Z is CH, or
U is $CH_2$, V is $NR^7$, W is CH, X is CH, Y is CH, and Z is N, or
U is $CH_2$, V is $NR^7$, W is CH, X is CH, Y is N, and Z is CH, or
U is $CH_2$, V is $NR^7$, W is CH, X is N, Y is CH, and Z is N; and
wherein $R^1$ to $R^7$ are as defined in any of the combinations given above.

In a certain embodiment the compounds of the invention are those compounds of formula (I-g), namely wherein U is C=O, V is $NR^7$; and one or two of the variables W, X, Y, and Z are nitrogen, the remaining variables being $CR^8$, wherein $R^1$ to $R^8$ are as defined in any of the combinations given above.

In a certain embodiment the compounds of the invention are those compounds of formula (I-g) wherein U is C=O, V is $NR^7$; and one of the variables W, X, Y, and Z is nitrogen, the remaining variables being $CR^8$, wherein $R^1$ to $R^8$ are as defined in any of the combinations given above.

In a certain embodiment the compounds of the invention are those compounds of formula (I-g) wherein
U is C=O, V is $NR^7$, W is N, X is CH, Y is CH, and Z is CH, or
U is C=O, V is $NR^7$, W is CH, X is N, Y is CH, and Z is CH, or
U is C=O, V is $NR^7$, W is CH, X is CH, Y is N, and Z is CH, or
U is C=O, V is $NR^7$, W is CH, X is CH, Y is CH, and Z is N, or
U is C=O, V is $NR^7$, W is N, X is CH, Y is N, and Z is CH, or
U is C=O, V is $NR^7$, W is N, X is CH, Y is CH, and Z is N, or
U is C=O, V is $NR^7$, W is CH, X is N, Y is N, and Z is CH, or
U is C=O, V is $NR^7$, W is CH, X is N, Y is CH, and Z is N; and
wherein $R^1$ to $R^7$ are as defined in any of the combinations given above.

In a certain embodiment the compounds of the invention are those compounds of formula (I-h), namely wherein
U is C=O, V is O; and one or two of the variables W, X, Y, and Z are nitrogen, the remaining variables being $CR^8$, wherein $R^1$ to $R^6$ and $R^8$ are as defined in any of the combinations given above.

In a certain embodiment the compounds of the invention are those compounds of formula (I-h) wherein
U is C=O, V is O; and one of the variables W, X, Y, and Z is nitrogen, the remaining variables being $CR^8$, wherein $R^1$ to $R^6$ and $R^8$ are as defined in any of the combinations given above.

In a certain embodiment the compounds of the invention are those compounds of formula (I-h) wherein
U is C=O, V is O, W is N, X is CH, Y is CH, and Z is CH, or
U is C=O, V is O, W is CH, X is N, Y is CH, and Z is CH, or
U is C=O, V is O, W is CH, X is CH, Y is N, and Z is CH, or
U is C=O, V is O, W is CH, X is CH, Y is CH, and Z is N, or
U is C=O, V is O, W is N, X is CH, Y is N, and Z is CH, or
U is C=O, V is O, W is N, X is CH, Y is CH, and Z is N, or
U is C=O, V is O, W is CH, X is N, Y is N, and Z is CH, or
U is C=O, V is O, W is CH, X is N, Y is CH, and Z is N; and wherein $R^1$ to $R^6$ are as defined in any of the combinations given above.

The invention further encompasses an embodiment of formula (I)

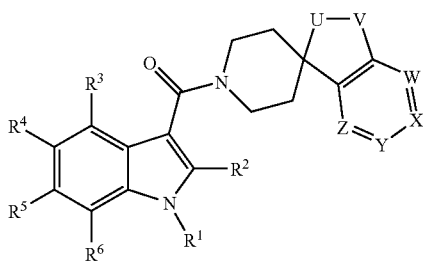

wherein
U is O, and V is $CH_2$,
U is O, and V is C=O,
U is $CH_2$, and V is O,
U—V is —CH=CH—,
U—V is —$CH_2$—$CH_2$—,
U is $CH_2$, V is $NR^7$;
U is C=O, and V is $NR^7$, or
U is C=O and V is O;
one or two of the variables W, X, Y and Z are nitrogen, the remaining variables being $CR^8$;
$R^1$ is H,
$C_{2-6}$-alkyl, optionally substituted with CN or OH,
$C_{1-6}$-haloalkyl,
—$(CR^iR^{ii})_mR^a$,
wherein $R^i$ and $R^{ii}$ are independently from each other H, methyl, or ethyl;
wherein m is from 0 to 4;
wherein $R^a$ is
phenyl, 5- to 6-membered heteroaryl, 3- to 7-membered heterocycloalkyl or 3 to 7-membered cyloalkyl,
which are optionally substituted with one or more A, or
—$NR^bR^c$, wherein $R^b$ and $R^c$ are each independently hydrogen, $C_{1-6}$-alkyl, —$S(O)_2$—$C_{1-6}$-alkyl, or —C(O)—$C_{1-6}$-alkyl, —$(CR^{iii}R^{iv})_n$—$C(O)R^d$
wherein $R^{iii}$ and $R^{iv}$ are independently from each other H, methyl, or ethyl;
wherein n is from 0 to 4;
wherein $R^d$ is
$C_{1-6}$-alkoxy,
—$NR^eR^f$, wherein $R^e$ and $R^f$ are each independently hydrogen,
$C_{1-6}$-alkyl, or
—$(C_{2-6}$-alkylene)-$NR^gR^h$; wherein $R^g$ and $R^h$ are each independently hydrogen, $C_{1-6}$-alkyl, or —C(O)O—$C_{1-6}$-alkyl, or
phenyl, 5- to 6-membered heteroaryl, 3- to 7-membered heterocycloalkyl or 3 to 7-membered cyloalkyl,
which are optionally substituted with one or more A,
—$S(O)_2$—$C_{1-6}$-alkyl,
—$S(O)_2N(C_{1-6}$-alkyl)$_2$, or
—$S(O)_2NH(C_{1-6}$-alkyl);
A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —$S(O)_{0-2}C_{1-16}$-alkyl, nitro, hydroxy, cyano, —($C_{1-6}$-alkylene)-O—$C_{1-6}$-alkyl, —($C_{1-6}$-alkylene)-O—$C_{1-6}$-haloalkyl, —($C_{1-6}$-alkylene)-OR''', —C(O)O$C_{1-6}$-alkyl, —C(O)$C_{1-6}$-alkyl, —C(O)OR''', —C(O)R''', —C(O)NR'R'', —$S(O)_2$NR'R'', —($CH_2$), —NR'R'', —($CH_2$), —NR'C(O)—$C_{1-6}$-alkyl, —($CH_2$), —NR'S(O)$_2$—$C_{1-6}$-alkyl, —$(CH_2)_x$—$C_{3-6}$-cycloalkyl, or —$(CH_2)_x$—R''',
wherein x is from 0 to 4,
R' and R'' are each independently H or $C_{1-6}$-alkyl, or
R' and R'' together with the nitrogen to which they are bound form a 5 or 6-membered heterocycle comprising one or two heteroatoms selected from N, O and S, and
R''' is phenyl or 5- to 6-membered heteroaryl, optionally substituted with one, two, or three halo, $C_{1-6}$-haloalkyl, $C_{1-6}$-alkyl, or $C_{1-6}$-alkoxy,
$R^2$ is hydrogen or $C_{1-6}$-alkyl;
$R^3$ and $R^6$ are hydrogen;
$R^4$ is hydrogen, Cl, F or methyl;
$R^5$ is hydrogen, halo, $CF_3$, methoxy or —$OCF_3$;
$R^7$ is hydrogen or $C_{1-6}$-alkyl;
$R^8$ is hydrogen;
or a pharmaceutically acceptable salt thereof.
Preferably, $R^1$ to $R^6$ are not simultaneously hydrogen.

The invention further encompasses an embodiment of formula (I)

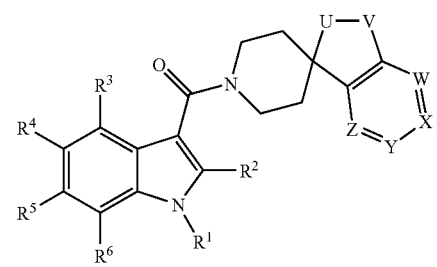

wherein
U is O, and V is $CH_2$,
U is O, and V is C=O,
U is $CH_2$, and V is O,
U—V is —CH=CH—,
U—V is —$CH_2$—$CH_2$—, U is CH$_2$, V is NR$^7$;
U is C=O, and V is NR$^7$, or
U is C=O and V is O;
one or two of the variables W, X, Y and Z are nitrogen, the remaining variables being CR$^8$;
R$^1$ is H,
  C$_{2-6}$-alkyl, optionally substituted with CN or OH,
  C$_{1-6}$-haloalkyl,
  —(CR$^i$R$^{ii}$)$_m$—R$^a$,
    wherein R$^i$ and R$^{ii}$ are independently from each other H, methyl, or ethyl;
    wherein m is from 1 to 4;
    wherein R$^a$ is
      phenyl, 5- to 6-membered heteroaryl, 3- to 7-membered heterocycloalkyl or 3 to 7-membered cyloalkyl,
        which are optionally substituted with one or more A, or
      —NR$^b$R$^c$, wherein R$^b$ and R$^c$ are each independently hydrogen, C$_{1-6}$-alkyl, —S(O)$_2$—C$_{1-6}$-alkyl, or —C(O)—C$_{1-6}$-alkyl,
  —(CR$^{iii}$R$^{iv}$)$_n$—C(O)R$^d$,
    wherein R$^{iii}$ and R$^{iv}$ are independently from each other H, methyl, or ethyl;
    wherein n is from 0 to 4;
    wherein R$^d$ is
      C$_{1-6}$-alkoxy,
      —NR$^e$R$^f$, wherein R$^e$ and R$^f$ are each independently hydrogen,
        C$_{1-6}$-alkyl, or
        —(C$_{2-6}$-alkylene)-NR$^g$R$^h$; wherein R$^g$ and R$^h$ are each independently hydrogen, C$_{1-6}$-alkyl, or —C(O)O—C$_{1-6}$-alkyl, or
      phenyl, 5- to 6-membered heteroaryl, 3- to 7-membered heterocycloalkyl or 3 to 7-membered cyloalkyl,
        which are optionally substituted with one or more A,
  —S(O)$_2$—C$_{1-6}$-alkyl,
  —S(O)$_2$N(C$_{1-6}$-alkyl)$_2$, or
  —S(O)$_2$NH(C$_{1-6}$-alkyl);

A is halo, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, C$_{1-6}$-thioalkyl, —S(O)$_2$—C$_{1-6}$-alkyl, cyano, —CH$_2$OCH$_3$, —C(O)O—C$_{1-6}$-alkyl, —C(O)NR'R", —S(O)$_2$NR'R", —NR'C(O)—C$_{1-6}$-alkyl, —NR'S(O)$_2$—C$_{1-6}$-alkyl, benzyl, or phenyl
  wherein R' and R" are each independently H or C$_{1-6}$-alkyl,
R$^2$ is hydrogen or C$_{1-6}$-alkyl;
R$^3$ and R$^6$ are hydrogen;
R$^4$ is hydrogen, Cl, F or methyl;
R$^5$ is hydrogen, halo, CF$_3$, methoxy or —OCF$_3$;
R$^7$ is hydrogen or C$_{1-6}$-alkyl;
R$^8$ is hydrogen;
or a pharmaceutically acceptable salt thereof.
  Preferably, R$^1$ to R$^6$ are not simultaneously hydrogen.
  The invention further encompasses an embodiment of formula (I)

wherein
U is O, V is CH$_2$, W is N, X is CH, Y is CH, and Z is CH,
U is O, V is CH$_2$, W is CH, X is CH, Y is N, and Z is CH, or
U is O, V is CH$_2$, W is CH, X is CH, Y is CH, and Z is N; and
R$^1$ is H,
  —CH$_2$—R$^a$,
    wherein R$^a$ is
      phenyl, or 5-membered heterocycloalkyl,
        which are optionally substituted with one or more halo, C$_{1-6}$-alkyl, or —C(O)O—C$_{1-6}$-alkyl;
R$^2$ is hydrogen;
R$^3$, R$^4$ and R$^6$ are hydrogen;
R$^5$ is Cl;
R$^8$ is hydrogen;
or a pharmaceutically acceptable salt thereof.
  Preferred compounds of formula (I-a), wherein W is N and X, Y and Z are CH, are

| Compound No. | Name |
| --- | --- |
| 1 | 1'-[(6-Chloro-1H-indol-3-yl)carbonyl]-7H-spiro[furo[3,4-b]pyridine-5,4'-piperidine] |
| 2 | tert-Butyl (2S)-2-{[6-chloro-3-(1'H,7H-spiro[furo[3,4-b]pyridine-5,4'-piperidin]-1'-ylcarbonyl)-1H-indol-1-yl]methyl}pyrrolidine-1-carboxylate |
| 3 | 1'-({6-Chloro-1-[(2S)-pyrrolidin-2-ylmethyl]-1H-indol-3-yl}carbonyl)-7H-spiro[furo[3,4-b]pyridine-5,4'-piperidine] dihydrochloride |
| 4 | 1'-[(6-Chloro-1-{[(2S)-1-methylpyrrolidin-2-yl]methyl}-1H-indol-3-yl)carbonyl]-7H-spiro[furo[3,4-b]pyridine-5,4'-piperidine] |
| 5 | 1'-{[6-Chloro-1-(3,5-difluorobenzyl)-1H-indol-3-yl]carbonyl}-7H-spiro[furo[3,4-b]pyridine-5,4'-piperidine] |

Preferred compounds of formula (I-a), wherein Z is N and W, X and Y are CH, are

| Compound No. | Name |
|---|---|
| 6 | 1'-[(6-Chloro-1H-indol-3-yl)carbonyl]-5H-spiro[furo[3,4-b]pyridine-7,4'-piperidine] |
| 7 | tert-Butyl (2S)-2-{[6-chloro-3-(1'H,5H-spiro[furo[3,4-b]pyridine-7,4'-piperidin]-1'-ylcarbonyl)-1H-indol-1-yl]methyl}pyrrolidine-1-carboxylate |
| 8 | 1'-({6-Chloro-1-[(2S)-pyrrolidin-2-ylmethyl]-1H-indol-3-yl}carbonyl)-5H-spiro[furo[3,4-b]pyridine-7,4'-piperidine] dihydrochloride |
| 9 | 1'-[(6-Chloro-1-{[(2S)-1-methylpyrrolidin-2-yl]methyl}-1H-indol-3-yl)carbonyl]-5H-spiro[furo[3,4-b]pyridine-7,4'-piperidine] |
| 14 | 1'-{[6-Chloro-1-(3,5-difluorobenzyl)-1H-indol-3-yl]carbonyl}-5H-spiro[furo[3,4-b]pyridine-7,4'-piperidine] |

Preferred compounds of formula (I-a), wherein Y is N and W, X and Z are CH, are

| Compound No. | Name |
|---|---|
| 10 | 1'-[(6-Chloro-1H-indol-3-yl)carbonyl]-1H-spiro[furo[3,4-c]pyridine-3,4'-piperidine] |
| 11 | tert-Butyl (2S)-2-{[6-chloro-3-(1H,1'H-spiro[furo[3,4-c]pyridine-3,4'-piperidin]-1'-ylcarbonyl)-1H-indol-1-yl]methyl}pyrrolidine-1-carboxylate |
| 12 | 1'-({6-Chloro-1-[(2S)-pyrrolidin-2-ylmethyl]-1H-indol-3-yl}carbonyl)-1H-spiro[furo[3,4-c]pyridine-3,4'-piperidine] dihydrochloride |
| 13 | 1'-[(6-Chloro-1-{[(2S)-1-methylpyrrolidin-2-yl]methyl}-1H-indol-3-yl)carbonyl]-1H-spiro[furo[3,4-c]pyridine-3,4'-piperidine] |

The invention also encompasses methods for treating dysmenorrhea, hypertension, chronic heart failure, inappropriate secretion of vasopressin, liver cirrhosis, nephrotic syndrome, obsessive compulsive disorder, anxiety and depressive disorders which comprise administering a therapeutically effective amount of a compound of formula (I), (I-a), (I-b), (I-c), (I-d), (I-e), (I-f), (I-g) or (I-h).

The invention also encompasses a pharmaceutical composition comprising a compound of formula (I), (I-a), (I-b), (I-c), (I-d), (I-e), (I-f), (I-g) or (I-h) and a pharmaceutically acceptable carrier. The pharmaceutical composition may further comprise at least one pharmaceutically acceptable excipient.

In a certain embodiment, the compounds of formula (I) of the invention can be manufactured according to a process comprising reacting a compound of formula (II):

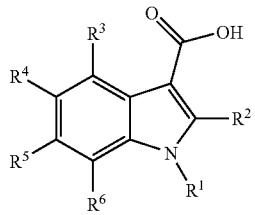

II with a compound of formula (III):

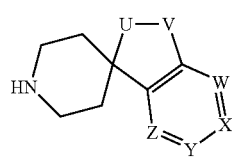

III to obtain a compound of formula (I) wherein $R^1$, $R^2$, $R^3$, $R^4$, $R^5$, $R^6$, U, V, W, X, Y and Z are as defined hereinabove for formula (I).

In another embodiment, the compounds of formula (I) of the invention can be manufactured according to a process comprising reacting a compound of formula (I-1), wherein $R^1$ equals H:

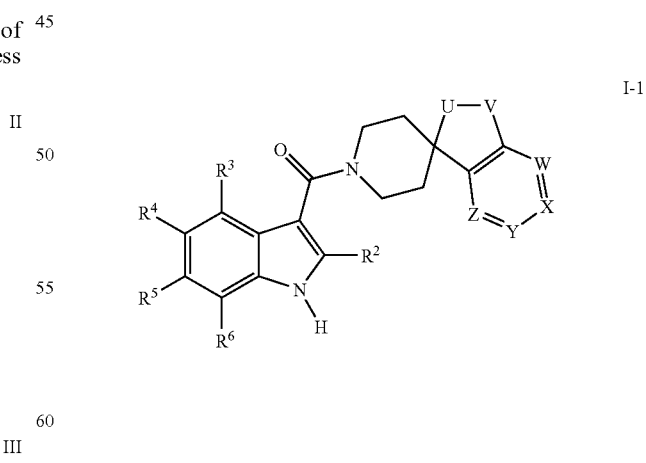

I-1 with a compound of formula $R^1$-LG (wherein $R^1$ is different from H), to obtain a compound of formula (I) wherein $R^1$, $R^2$, $R^3$, $R^4$, $R^5$, $R^6$, U, V, W, X, Y and Z are as defined hereinabove for formula (I), LG is halogen, —OS(O)$_2$Me or —OS(O)$_2$C$_6$H$_4$—CH$_3$, and with the proviso that $R^1$ is not H.

These processes are described in more detail with the following general schemes and procedures A to D.

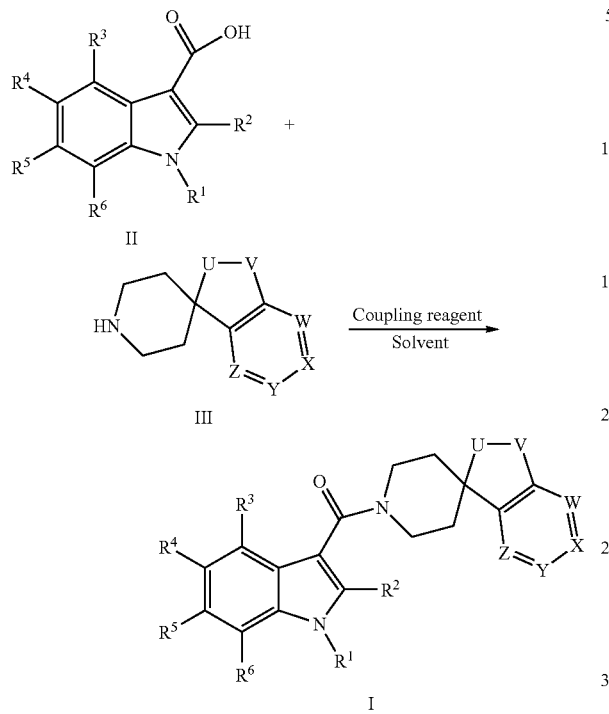

General scheme A available or prepared using methods known in the art starting from materials. Alternatively, they can be prepared following the general scheme D as described hereinafter. General scheme A is hereinafter further illustrated with general procedures IA, IB, II and III.

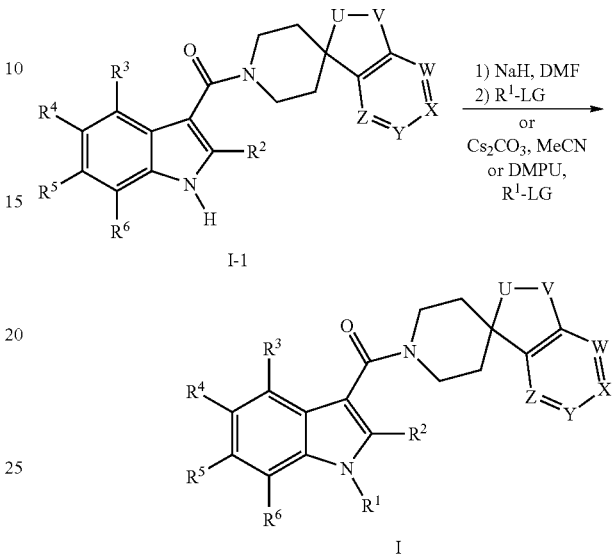

General scheme B

LG = leaving group, e.g. halogen, OSO$_2$Me or OSO$_2$C$_6$H$_4$CH$_3$

General Procedure A

Compounds of formula (I) can be prepared via an amide coupling between an indole 3-carboxylic acid (II) and a compound of formula (III). The usual reagents and protocols known in the art can be used to effect the amide coupling. Indole 3-carboxylic acids (II) are either commercially available or readily prepared using a procedure described in *J. Med. Chem.* 1991, 34, 140. Alternatively, they can be prepared following the general scheme C as described hereinafter. The compounds of formula (III) are either commercially General Procedure B Compounds of formula (I) with R$^1$ different from H can be prepared using methods known in the art, e.g. by N-deprotonation of a compound of formula (I-1) (compounds of formula (I) wherein R$^1$ is H) followed by treatment with an electrophilic reactant R$^1$-LG (wherein LG is a leaving group, e.g. halogen or sulfonyl) which is either commercially available or easily prepared according to methods well known in the art and starting materials. General scheme B is hereinafter further illustrated with general procedure IV.

General scheme C

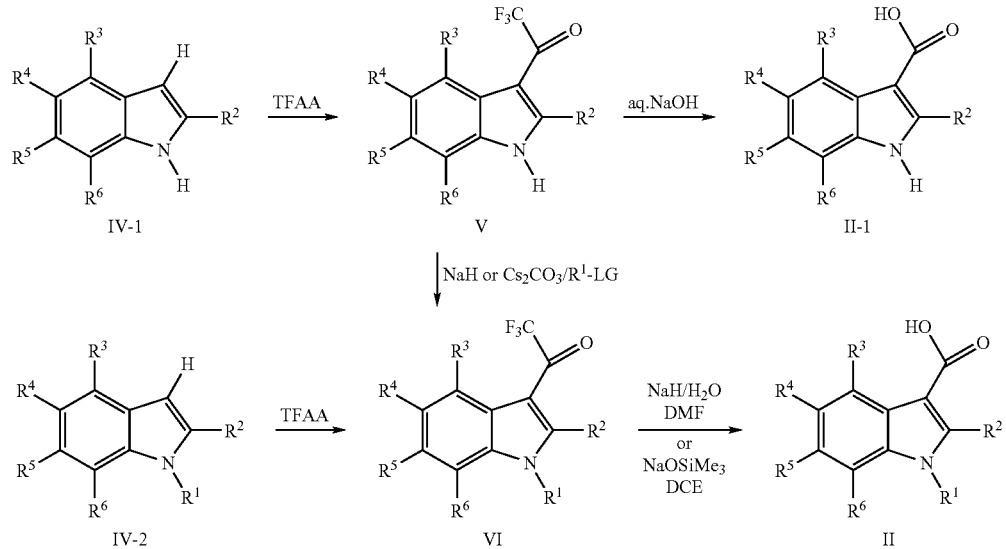

LG = leaving group, e.g. halogen, OSO$_2$Me or OSO$_2$C$_6$H$_4$CH$_3$

General Procedure C

The treatment of an indole derivative (IV-1) with trifluoroacetic anhydride in DMF affords intermediate (V) which can be hydrolysed with an aqueous sodium hydroxide solution to give the 3-carboxylic acid indole derivative (II-1). Alternatively, (V) could react with an electrophilic reactant $R^1$-LG to give (VI), which is then converted to the corresponding carboxylic acid derivative (II) with $NaH/H_2O$ in DMF (see *J. Org Chem.*, 1993, 10, 2862). Intermediate (VI) can alternatively be obtained by treatment of an indole derivative (IV-2) with trifluoroacetic anhydride in a suitable solvent, e.g. DMF, dichloromethane or 1,2-dichloroethane. Addition of a suitable base may be advantageous.

hydrogen gas in the presence of palladium on charcoal, to give compounds of formula (III-2), or reduced using a stepwise procedure by consecutive treatment with diisopropylaluminum hydride, acetic anhydride in the presence of pyridine and 4-N,N-dimethylaminopyridine, and triethylsilane in the presence of boron trifluoride to yield compounds of formula (XI). Compounds of formula (XI) can be N-debenzylated under hydrogenolytic conditions, e.g. using hydrogen gas in the presence of palladium on charcoal, to give compounds of formula (III-1).

The compounds of the present invention exhibit V1a activity, which may be detected as described below:

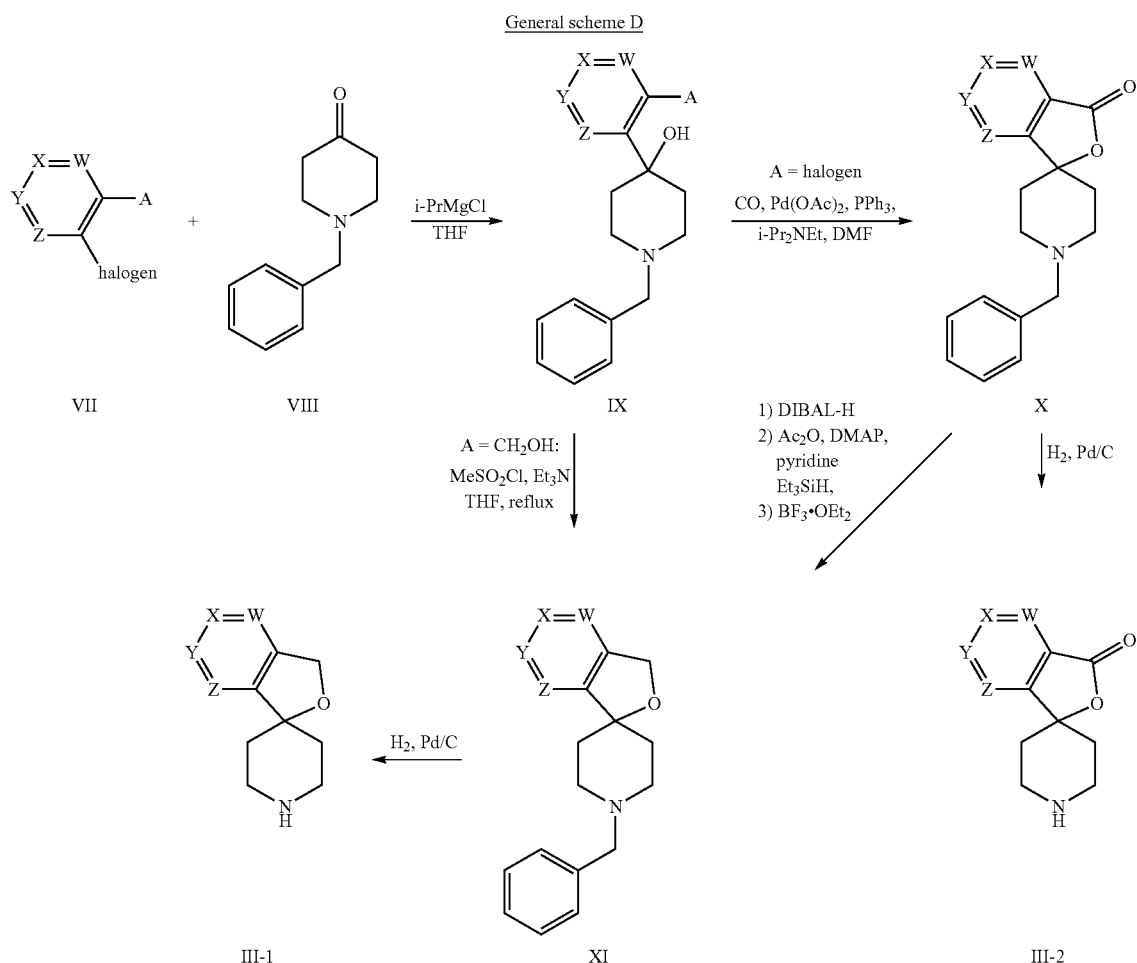

General scheme D

General Procedure D

Treatment of compounds of formula (VII) with isopropyl magnesium chloride leads to the formation of a Grignard reagent which is added to the carbonyl moiety of 1-benzyl-4-piperidone (VIII) to form compounds of formula (IX). Treatment of a compound of formula (IX) with methanesulfonyl chloride in the presence of an amine base such as triethylamine gives rise to spiropiperidine derivatives of formula (XI). Alternatively, compounds of formula (IX) can be treated with carbon monoxide in the presence of a palladium catalyst, e.g. formed in situ from palladium acetate and triphenylphosphine, and an amine base to form spirolactone compounds of formula (X). Compounds of formula (X) can either be N-debenzylated under hydrogenolytic conditions, e.g. using

V1a Activity

Material & Method:

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells were resuspended in 30 ml freshly prepared ice cold Lysis buffer (50 mM HEPES, 1 mM EDTA, 10 mM $MgCl2$ adjusted to pH=7.4+complete cocktail of protease inhibitor (Roche Diagnostics)); homogenized with Polytron for 1 min, and sonicated on ice for 2×2 minutes at 80% intensity (Vibracell sonicator). The preparation was centrifuged 20 min at 500 g at 4° C., the pellet was discarded and the supernatant centrifuged 1 hour at 43'000 g at 4° C. (19'000 rpm). The pellet was resuspended in 12.5 ml Lysis buffer+ 12.5 ml Sucrose 20% and homogenized using a Polytron for 1-2 min. The protein concentration was determined by the Bradford method and aliquots were stored at −80° C. until use. For binding studies 60 mg Yttrium silicate SPA beads (Amersham) were mixed with an aliquot of membrane in binding buffer (50 mM Tris, 120 mM NaCl, 5 mM KCl, 2 mM CaCl2, 10 mM MgCl2) for 15 minutes with mixing. 50 ul of bead/membrane mixture was then added to each well of a 96 well plate, followed by 50 ul of 4 nM 3H-Vasopressin (American Radiolabeled Chemicals). For total binding measurement 100 ul of binding buffer were added to the respective wells, for non-specific binding 100 ul of 8.4 mM cold vasopressin and for compound testing 100 ul of a serial dilution of each compound in 2% DMSO. The plate was incubated 1 h at room temperature, centrifuged 1 min at 1000 g and counted on a Packard Top-Count. Non-specific binding counts wee subtracted from each well and data was normalized to the maximum specific binding set at 100%. To calculate an IC 50 the curve was fitted using a non-linear regression model (XLfit), and the Ki was calculated using the Cheng-Prussoff equation.

| Compound No | pKi (hV1a) |
|---|---|
| 3 | 7.60 |
| 4 | 8.81 |
| 5 | 8.36 |
| 6 | 8.28 |
| 7 | 7.64 |
| 8 | 8.48 |
| 9 | 9.00 |
| 10 | 8.06 |
| 11 | 7.63 |
| 12 | 8.34 |
| 13 | 8.96 |
| 14 | 8.37 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions. The pharmaceutical compositions of the invention, in addition to one or more compounds of the invention, for example compounds of formulae (I-a) to (I-h), contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula (I) should be appropriate, although the above upper limit can also be exceeded when necessary.

The following Examples illustrate the present invention without limiting it. All temperatures are given in degrees Celsius.

Example A

Tablets of the following composition can be manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition can be manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch can be firstly mixed in a mixer and then in a comminuting machine. The mixture can be returned to the mixer, the talc can be added thereto and mixed thoroughly. The mixture can be filled by machine into hard gelatine capsules.

Example C

Suppositories of the following composition can be manufactured:

|  | mg/supp. |
|---|---|
| Active substance | 15 |
| Suppository mass | 1285 |
| Total | 1300 |

The suppository mass can be melted in a glass or steel vessel, mixed thoroughly and cooled to 45° C.

Thereupon, the finely powdered active substance can be added thereto and stirred until it has dispersed completely. The mixture can be poured into suppository moulds of suitable size, left to cool; the suppositories then can be removed from the moulds and packed individually in wax paper or metal foil.

In the following, the synthesis of compounds of formula (I) is further exemplified: The compounds of formula I may be prepared in accordance with the process variants as described above. The starting materials described in the Example section are either commercially available or are otherwise known or derived from the chemical literature, for instance as cited below, or may be prepared as described in the Examples section.

Examples

Acid Intermediates of Formula II and II-1

Acid 1

6-Chloro-1H-indole-3-carboxylic acid a) 1-(6-Chloro-1H-indol-3-yl)-2,2,2-trifluoro-ethanone

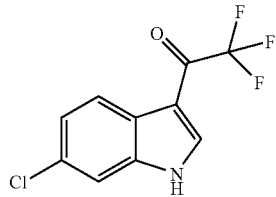

To a solution of 1.0 g (6.6 mmol) 6-chloroindole in 13 ml DMF were added dropwise at 0° C. 2.75 ml (19.8 mmol) trifluoroacetic anhydride. Stirring at this temperature for 90 min. was followed by quenching with 30 ml of a 2 M aqueous solution of sodium carbonate, dilution with 50 ml water and extraction with three 100-ml portions of tert-butyl methyl ether. The combined organic layers were dried over sodium sulfate, filtered and concentrated to give 1.3 g (80%) of the crude title compound as an off-white solid.

MS m/e (%): 246 (M–H$^+$).

b) 6-Chloro-1H-indole-3-carboxylic acid

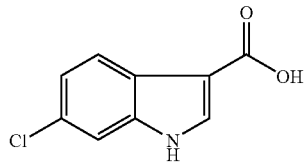

A mixture of 1.3 g (5.3 mmol) 1-(6-chloro-1H-indol-3-yl)-2,2,2-trifluoro-ethanone and 26.5 ml of a 4 M aqueous solution of sodium hydroxide was heated at reflux for 4.5 h. The mixture was cooled to room temperature and washed with two 100-ml portions of tert-butyl methyl ether. The aqueous layer was acidified to pH 2-3 by addition of concentrated hydrochloric acid solution at 0° C. Extraction with three 100-ml portions of tert-butyl methyl ether, drying over sodium sulfate, filtration and concentration in vacuo gave 0.80 g (78%) of the crude title compound as a brown solid.

MS m/e (%): 194 (M–H$^+$).

Acid 2

1-((S)-1-tert-Butoxycarbonyl-pyrrolidin-2-ylmethyl)-6-chloro-1H-indole-3-carboxylic acid a) (S)-2-[6-Chloro-3-(2,2,2-trifluoro-acetyl)-indol-1-ylmethyl]-pyrrolidine-1-carboxylic acid tert-butyl ester

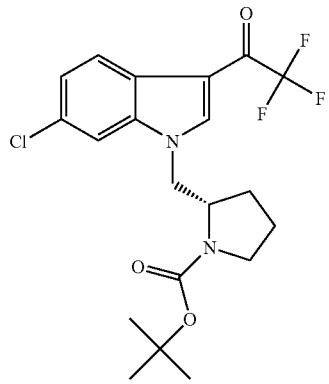

A mixture of 2.2 g (8.7 mmol) 1-(6-chloro-1H-indol-3-yl)-2,2,2-trifluoro-ethanone, 3.7 g (13 mmol) (S)-2-methanesulfonyloxymethyl-pyrrolidine-1-carboxylic acid tert-butyl ester (preparation described in Tetrahedron 2006, 62, 4584-4589) and 5.7 g (18 mmol) cesium carbonate in 44 ml dry 1,3-dimethyl-3,4,5,6-tetrahydropyrimidinone (DMPU) was stirred for 48 h at 80° C. The reaction mixture was diluted with 100 ml water and extracted with ethyl acetate (3×100 ml). The combined organic layers were dried over sodium sulfate and concentrated to dryness. Residual DMPU was removed by kugelrohrdistillation in high vacuo (ca. 1 mbar) at 120° C. Flash chromatography gave the title compound (1.7 g, 46%) as a light yellow solid.

MS m/e (%): 489 (M+CH$_3$CO$_2^-$, 100).

b) 1-((S)-1-tert-Butoxycarbonyl-pyrrolidin-2-ylmethyl)-6-chloro-1H-indole-3-carboxylic acid

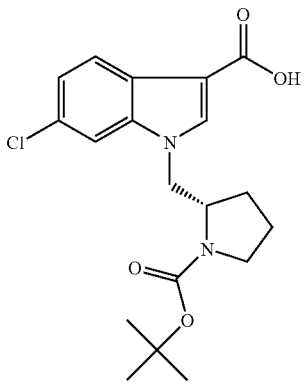

To a solution of 1.7 g (4.0 mmol) (S)-2-[6-chloro-3-(2,2,2-trifluoro-acetyl)-indol-1-ylmethyl]-pyrrolidine-1-carboxylic acid tert-butyl ester and 1.0 g (22 mmol) sodium hydride (50% in oil) in 40 ml dry N,N-dimethylformamide were added dropwise 0.36 ml (20 mmol) water under waterbath cooling. After stirring for 45 min the reaction mixture was diluted with 80 ml tert-butyl methyl ether. The organic layer was extracted with aqueous 1 M sodium hydroxide solution (2×100 ml). The combined aqueous layers were acidified to pH 2 with ice-cold aqueous hydrochloric acid solution and extracted with ethyl acetate (3×100 ml). The combined ethyl acetate layers were dried over sodium sulfate and concentrated to dryness to give the title compound (1.4 g, 96%) as a light yellow solid.

MS m/e (%): 377 (M−H$^+$, 100).

Acid 3

6-Chloro-1-(3,5-difluoro-benzyl)-1H-indole-3-carboxylic acid a) 1-[6-Chloro-1-(3,5-difluoro-benzyl)-1H-indol-3-yl]-2,2,2-trifluoro-ethanone

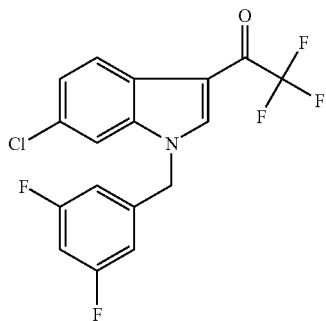

A mixture of 2.0 g (9.4 mmol) 1-(6-chloro-1H-indol-3-yl)-2,2,2-trifluoro-ethanone, 4.59 g (14.1 mmol) cesium carbonate and 2.14 g (10.4 mmol) 3,5-difluorobenzyl bromide in 90 ml acetonitrile was heated at 80° C. for 3 h. After cooling to room temperature addition of 150 ml water was followed by extraction with three 150-ml portions of tert-butyl methyl ether. The combined organic layers were dried over sodium sulfate, filtered and concentrated in vacuo. The residue was triturated in 30 ml hot cyclohexane. Filtration gave 2.2 g (64%) of the crude title compound as light brown solid.

MS m/e (%): 372 (M−H$^+$).

b) 6-Chloro-1-(3,5-difluoro-benzyl)-1H-indole-3-carboxylic acid

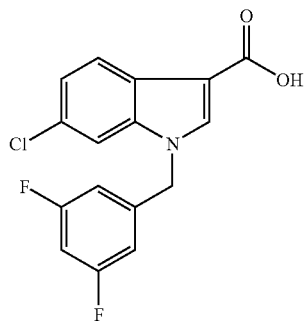

To a solution of 2.2 g (6.5 mmol) 1-[6-chloro-1-(3,5-difluoro-benzyl)-1H-indol-3-yl]-2,2,2-trifluoro-ethanone in 65 ml DMF were added 1.7 g (36 mmol) sodium hydride (50% in oil) at room temperature. After stirring for 5 min. 0.59 ml (33 mmol) water were added dropwise. Stirring was continued at room temperature for 45 min. The reaction mixture was diluted with 150 ml of tert-butyl methyl ether and extracted with two 150-ml portions of a 1 M aqueous solution of sodium hydroxide. The combined aqueous layers were acidified to pH 1 with concentrated hydrochloric acid solution and extracted with three 150-ml portions of ethyl acetate. The combined organic extracts were dried over sodium sulfate, filtered and concentrated in vacuo. The residue was dried in high vacuo at 80° C. to give 2.0 g (95%) of the crude title compound as a brown solid.

MS m/e (%): 320 (M−H$^+$).

Amine Intermediates of Formula III

Amine 1

7H-Spiro[furo[3,4-b]pyridine-5,4'-piperidine]

a) 1'-Benzyl-2-bromo-2',3',5',6'-tetrahydro-1'H-[3,4']bipyridinyl-4'-ol

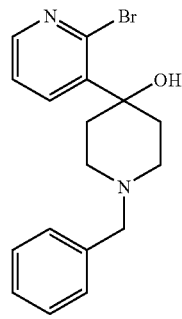

To a solution of 10 g (42 mmol) 2,3-dibromopyridine in 210 ml dry tetrahydrofuran at room temperature were added 22 ml (44 mmol) 2-propylmagnesium chloride solution (2.0 M in tetrahydrofuran). The reaction mixture was stirred for 1 h at room temperature. A solution of 7.9 g (44 mmol) 1-benzyl-4-piperidone in 40 ml tetrahydrofuran was added, and stirring was continued for 16 h. The reaction mixture was quenched with water, basified to pH 9 with aqueous 2 M sodium hydroxide solution and extracted with tert-butyl methyl ether (3×). The combined organic layers were washed with brine, dried over sodium sulfate and concentrated in vacuo. Flash-chromatography (aminopropyl-modified silica gel) gave the title compound (3.4 g, 23%) as an orange amorphous solid.

MS m/e (%): 349, 347 (M+H$^+$, 100, 97).

b) 1'-Benzyl-7H-spiro[furo[3,4-b]pyridine-5,4'-piperidin]-7-one

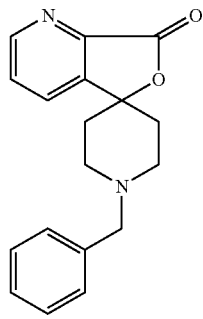

A mixture of 3.4 g (9.7 mmol) 1'-benzyl-2-bromo-2',3',5',6'-tetrahydro-1'H-[3,4']bipyridinyl-4'-ol, 3.3 ml (1.9 mmol) N,N-diisopropylethylamine, 0.22 g (1.0 mmol) Pd(II) acetate and 0.25 g (1.0 mmol) triphenylphosphine in 100 ml N,N-dimethylformamide was purged with carbon monoxide and stirred under an atmosphere of carbon monoxide at 80° C. for 72 h. The reaction mixture was diluted with tert-butyl methyl ether and washed with water (pH adjusted to 8 with saturated aqueous sodium bicarbonate solution). The aqueous layer was extracted with two portions of tert-butyl methyl ether. The combined organic layers were washed with two portions of water and brine, dried over sodium sulfate and concentrated to dryness. Flash-chromatography gave the title compound (1.2 g, 43%) as a yellow solid.

MS m/e (%): 295 (M+H$^+$, 100).

c) (RS)-1'-Benzyl-7H-spiro[furo[3,4-b]pyridine-5,4'-piperidin]-7-yl acetate

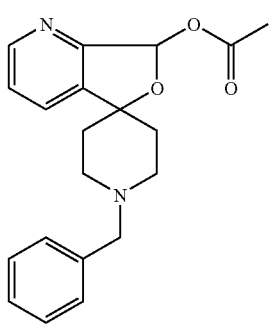

To a solution of 1.0 g (3.4 mmol) 1'-benzyl-7H-spiro[furo[3,4-b]pyridine-5,4'-piperidin]-7-one in 34 ml dichloromethane at −78° C. were added 6.8 ml (6.8 mmol) diisobutylaluminum hydride solution (1 M in n-hexane). After 45 min were subsequently added 0.80 ml (10 mmol) pyridine, a solution of 0.83 g (6.8 mmol) 4-N,N-dimethylaminopyridine in 2 ml dichloromethane and 1.9 ml (20 mmol) acetic anhydride. The reaction mixture was stirred at −78° C. for 14 h. The reaction was quenched with 34 ml aqueous saturated ammonium chloride solution and 26 ml 1 M aqueous sodium potassium tartrate solution and stirred for 30 min. Addition of saturated aqueous sodium hydrogen carbonate solution was followed by extraction with three portions of dichloromethane. The combined organic layers were dried over sodium sulfate and concentrated in vacuo. Flash-chromatography gave the title compound (0.8 g; 70%) as a light yellow solid.

MS m/e (%): 339 (M+H$^+$, 100).

d) 1'-Benzyl-7H-spiro[furo[3,4-b]pyridine-5,4'-piperidine]

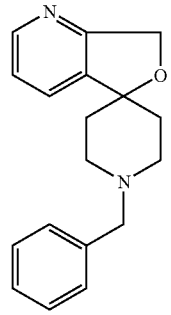

To a solution of 0.80 g (2.4 mmol) 1'-benzyl-7H-spiro[furo[3,4-b]pyridine-5,4'-piperidin]-7-yl acetate in 47 ml dichloromethane were subsequently added 2.8 ml (18 mmol) triethylsilane and 2.2 ml (18 mmol) boron trifluoride etherate at room temperature. The reaction mixture was heated at reflux over night. The cooling bath was then removed and the reaction mixture was diluted with dichloromethane. The organic layer was washed with aqueous 2 M sodium hydroxide solution. The aqueous layer was extracted with two portions of dichloromethane. The combined organic layers were dried over sodium sulfate and concentrated in vacuo. Flash-chromatography (aminopropyl-modified silica gel) gave the title compound (0.59 g, 89%) as a colorless oil.

MS m/e (%): 281 (M+H$^+$, 100).

e) 7H-Spiro[furo[3,4-b]pyridine-5,4'-piperidine]

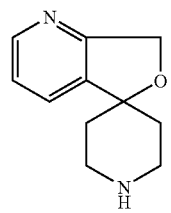

A 2-necked round bottom flask was charged with 0.56 g (2.0 mmol) 1'-benzyl-7H-spiro[furo[3,4-b]pyridine-5,4'-piperidine] and 20 ml 2,2,2-trifluoroethanol. The reaction mixture was purged with argon prior to adding 0.21 g (10 mol-%) palladium on activated charcoal. The flask was evacuated, refilled with hydrogen and stirred for 16 h. The catalyst was filtered off and washed with ethanol. The filtrate was concentrated to dryness to give the title compound (0.43 g, quantitative, purity of approx. 90%) as a light brown solid.

MS m/e (%): 191 (M+H$^+$, 100).

Amine 2

5H-Spiro[furo[3,4-b]pyridine-7,4'-piperidine]

a) (2-Bromo-pyridin-3-yl)-methanol

To a solution of 10 g (50 mmol) 2-bromonicotinic acid and 7.2 ml (52 mmol) triethylamine in 500 ml toluene at room temperature were added 5.0 ml (52 mmol) ethyl chloroformate. The reaction mixture was stirred for 1 h. The precipitate was filtered off and the filtrate was concentrated to dryness to give the mixed anhydride as a colorless oil. A solution of the mixed anhydride in 60 ml dry tetrahydrofuran was added dropwise to a suspension of 2.0 g (52 mmol) lithium aluminum hydride in 270 ml dry tetrahydrofuran at −70° C. The reaction mixture was stirred for 1 h and then quenched with 2.0 ml water, 2.0 ml aqueous 2 M sodium hydroxide and 6.0 ml water. The granular precipitate was filtered off and washed with ethyl acetate. The filtrate was concentrated to dryness to give the title compound (7.8 g, 84%) as an off-white solid.

MS m/e (%): 188 (93), 190 (100) (M+H$^+$).

b) 1'-Benzyl-3-hydroxymethyl-2',3',5',6'-tetrahydro-1'H-[2,4']bipyridinyl-4'-ol

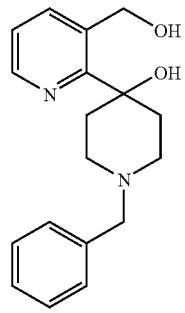

To a solution of 4.0 g (21 mmol) (2-bromo-pyridin-3-yl)-methanol in 105 ml dry tetrahydrofuran were added 22 ml (45 mmol) 2-propylmagnesium chloride solution (2.0 M in tetrahydrofuran). The reaction mixture was heated at reflux for 2 h. A solution of 3.8 g (21 mmol) 1-benzyl-4-piperidone in 22 ml tetrahydrofuran was added dropwise at a temperature of approximately 65° C. The reaction mixture was heated at reflux for 3 h and then quenched with water. The aqueous layer was basified to pH 9 with aqueous 1 M sodium hydroxide and extracted with three portions of ethyl acetate. The combined organic layers were washed with brine, dried over sodium sulfate and concentrated in vacuo. Flash-chromatography gave the title compound (1.1 g, 17%) as a brown solid.

MS m/e (%): 299 (M+H$^+$, 100).

c) 1'-Benzyl-5H-spiro[furo[3,4-b]pyridine-7,4'-piperidine]

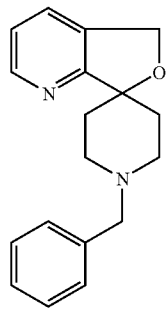

To a solution of 1.1 g (3.5 mmol) 1'-benzyl-3-hydroxymethyl-2',3',5',6'-tetrahydro-1'H-[2,4']bipyridinyl-4'-ol and 1.0 ml (7.4 mmol) triethylamine in 35 ml dry tetrahydrofuran were added 0.26 ml (3.3 mmol) methane sulfonyl chloride at room temperature. The reaction mixture was heated at reflux for 1 h and then quenched with water. The aqueous layer was basified with aqueous 1 M sodium hydroxide and extracted with three portions of ethyl acetate. The combined organic layers were dried over sodium sulfate and concentrated in vacuo. Flash-chromatography (aminopropyl-modified silica gel) gave the title compound (0.62 g, 62%) as a light yellow amorphous solid.

MS m/e (%): 281 (M+H$^+$, 100).

d) 5H-Spiro[furo[3,4-b]pyridine-7,4'-piperidine]

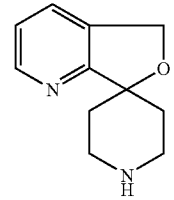

A solution of 0.39 g (1.4 mmol) 1'-benzyl-5H-spiro[furo[3,4-b]pyridine-7,4'-piperidine] in 14 ml ethanol was purged with argon prior to adding 0.15 g (10 mol %) palladium on activated charcoal. The flask was evacuated, refilled with hydrogen gas and stirred at room temperature under an atmosphere of hydrogen for 16 h. The catalyst was filtered off and washed with ethanol. The filtrate was concentrated to dryness to give the title compound (0.24 g, 91%) as an amorphous solid.

MS m/e (%): 191 (M+H$^+$, 100).

Amine 3

1H-Spiro[furo[3,4-c]pyridine-3,4'-piperidine]

a) (3-Bromo-pyridin-4-yl)-methanol

To a solution of 2.5 g (12 mmol) 3-bromo-4-pyridinecarboxylic acid and 1.8 ml (13 mmol) triethylamine in 120 ml toluene were added 1.2 ml (13 mmol) ethyl chloroformate at room temperature. The reaction mixture was stirred for 1 h. The precipitate was filtered off and the filtrate was concentrated to dryness to give the mixed anhydride as colorless oil. A solution of the mixed anhydride in 13 ml dry tetrahydrofuran was added dropwise to a suspension of 0.52 g (13 mmol) lithium aluminum hydride in 70 ml dry tetrahydrofuran at −70° C. The reaction mixture was stirred for 1 h and then quenched with 0.5 ml water, 0.5 ml aqueous 2 M sodium hydroxide and 1.5 ml water. The granular precipitate was filtered off and washed with ethyl acetate. The filtrate was concentrated to dryness to give the title compound (2.0 g, 85%) as a light brown solid.

MS m/e (%): 190, 188 (M+H$^+$, 100, 92).

b) 1'-Benzyl-4-hydroxymethyl-2',3',5',6'-tetrahydro-1'H-[3,4']bipyridinyl-4'-ol

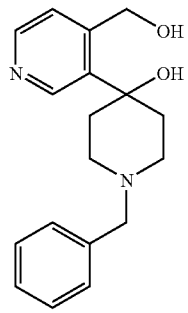

To a solution of 1.9 g (10 mmol) (3-bromo-pyridin-4-yl)-methanol in 50 ml dry tetrahydrofuran were added 11 ml (21 mmol) 2-propylmagnesium chloride solution (2.0 M in tetrahydrofuran). The reaction mixture was heated at reflux for 2 h. A solution of 1.9 g (10 mmol) 1-benzyl-4-piperidone in 5 ml tetrahydrofuran was added dropwise at a temperature of approximately 65° C. The reaction mixture was heated at reflux for 2 h and then quenched with water. The tetrahydrofuran was evaporated. The aqueous layer was basified to pH 10 with aqueous 2 M sodium hydroxide solution and extracted with three portions of tert-butyl methyl ether. The combined organic layers were washed with brine, dried over sodium sulfate and concentrated in vacuo. Flash-chromatography gave the title compound (0.47 g, 16%) as a brown solid.

MS m/e (%): 299 (M+H$^+$, 100).

c) 1'-Benzyl-1H-spiro[furo[3,4-c]pyridine-3,4'-piperidine]

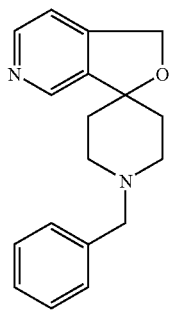

To a solution of 0.46 g (1.5 mmol) 1'-benzyl-4-hydroxymethyl-2',3',5',6'-tetrahydro-1'H-[3,4']bipyridinyl-4'-ol and 0.45 ml (3.2 mmol) triethylamine in 15 ml dry tetrahydrofuran at were added 0.11 ml (1.5 mmol) methane sulfonyl chloride room temperature. The reaction mixture was heated at reflux for 1 h and then quenched with water. The aqueous layer was basified with aqueous 1 M sodium hydroxide and extracted with three portions of ethyl acetate. The combined organic layers were dried over sodium sulfate and concentrated in vacuo. Flash-chromatography (aminopropyl-modified silica gel) gave the title compound (0.52 g, 57%) as a light yellow amorphous solid.

MS m/e (%): 281 (M+H$^+$, 100).

d) 1H-Spiro[furo[3,4-c]pyridine-3,4'-piperidine]

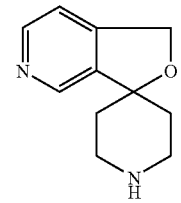

A solution of 0.22 g (0.78 mmol) 1'-benzyl-1H-spiro[furo[3,4-c]pyridine-3,4'-piperidine] in 8 ml 2,2,2-trifluoroethanol was purged with argon prior to adding 0.08 g (10 mol %) palladium on activated charcoal. The flask was evacuated, refilled with hydrogen gas and stirred under an atmosphere of hydrogen gas for 20 h. The catalyst was filtered off and washed with ethanol. The filtrate was concentrated to dryness to give the title compound (0.16 g, quantitative, purity of approximately 95%) as a light yellow amorphous solid.

MS m/e (%): 191 (M+H$^+$, 100).

Examples

Amide Coupling

General Procedure IA:

To a 0.1 M solution of an indole-3-carboxylic acid derivative (1 mmol) in dichloromethane are added few drops of N,N-dimethylformamide and oxalyl chloride (1.25 mmol) at 0° C. The mixture is allowed to warm to room temperature and stirred for 2 h. After adding a 1 M solution of the amine derivative (1.1 mmol) and N,N-diisopropylethylamine (2.2 mmol) in dichloromethane the mixture is stirred for 1 h at room temperature. Quenching with water and basification with 1 M aqueous sodium hydroxide solution are followed by extraction with three portions of ethyl acetate. The combined organic layers are dried over sodium sulfate and concentrated. Purification by flash chromatography (silica gel or aminopropyl-modified silica gel) yields an amide derivative of formula (I).

General Procedure IB:

To a 0.1 M solution of an indole-3-carboxylic acid derivative (1 mmol) and N,N-diisopropylethylamine (1.1 mmol) in dichloromethane are added few drops of N,N-dimethylformamide and oxalyl chloride (1.25 mmol) at 0° C. The mixture is allowed to warm to room temperature and stirred for 2 h. After adding a 1 M solution of the amine derivative (1.1 mmol) and N,N-diisopropylethylamine (1.1 mmol) in dichloromethane the mixture is stirred for 1 h at room temperature. Quenching with water and basification with 1 M aqueous sodium hydroxide solution are followed by extraction with three portions of ethyl acetate. The combined organic layers are dried over sodium sulfate and concentrated. Purification by flash chromatography (silica gel or aminopropyl-modified silica gel) yields an amide derivative of formula (I).

General Procedure II:

To a stirred solution of an indole-3-carboxylic acid derivative (1 mmol) in 10 ml CH$_2$Cl$_2$ are added (1.3 mmol) EDC, (1.3 mmol) HOBt, (1.3 mmol) triethylamine and (1 mmol) of the amine derivative. The mixture is stirred overnight at RT and then poured onto water and extracted with CH$_2$Cl$_2$. The combined organic phases are dried over Na$_2$SO$_4$ and concentrated in vacuo. Flash chromatography or preparative HPLC affords an amide derivative of formula (I).

General Procedure III:

To a solution of an indole-3-carboxylic acid derivative (0.13 mmol), N,N-diisopropylethylamine (0.14 mmol) and TBTU or HATU (0.14 mmol) in 2 ml dry N,N-dimethylformamide is added the amine derivative (0.14 mmol) at RT. The reaction mixture is quenched with 0.5 M aqueous sodium hydroxide (20 ml) after 2 h and extracted with three portions of ethyl acetate. The combined organic layers are washed with water and brine, dried over sodium sulfate and concentrated to dryness. Flash chromatography or preparative HPLC affords an amide derivative of formula (I).

Indole-N-Alkylation:
General Procedure IV:

To a stirred solution of an indole of formula (I-1) wherein $R^1$ is H in DMF are added 2. 1 eq. NaH (60% in oil). The mixture is stirred at RT for 30 min. and then the electrophilic reagent $R^1$-LG (1.1 eq.) is added. The mixture is stirred an additional 14 hours at 60° C. and then poured onto water and extracted with ethyl acetate. The combined organic phases are dried over $Na_2SO_4$ and concentrated in vacuo. Purification by preparative HPLC affords compounds of formula (I) with $R^1$ different from H.

Example 1

1'-[(6-Chloro-1H-indol-3-yl)carbonyl]-7H-spiro[furo[3,4-b]pyridine-5,4'-piperidine]

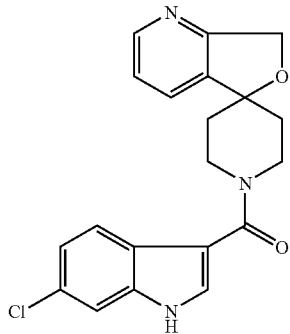

The title compound was obtained as a light brown solid in 96% yield according to the amide coupling procedure described in general procedure IA.
Acid: 6-Chloro-1H-indol-3-carboxylic acid
Amine: 7H-Spiro[furo[3,4-b]pyridine-5,4'-piperidine]
MS m/e (%): 368 (M+H$^+$, 100).

Example 2 tert-Butyl (2S)-2-{[6-chloro-3-(1'H,7H-spiro[furo[3,4-b]pyridine-5,4'-piperidin]-1'-ylcarbonyl)-1H-indol-1-yl]methyl}pyrrolidine-1-carboxylate

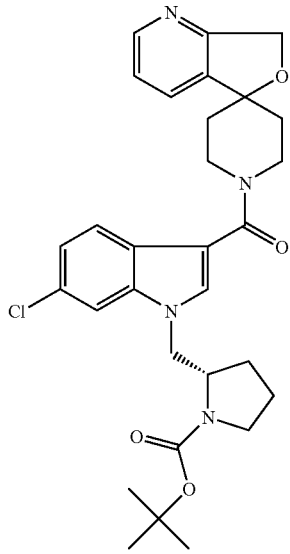

The title compound was obtained as an off-white solid in 90% yield according to the amide coupling procedure described in general procedure IB.
Acid: 1-((S)-1-tert-Butoxycarbonyl-pyrrolidin-2-ylmethyl)-6-chloro-1H-indole-3-carboxylic acid
Amine: 7H-Spiro[furo[3,4-b]pyridine-5,4'-piperidine]
MS m/e (%): 551 (M+H$^+$, 76).

Example 3

1'-({6-Chloro-1-[(2S)-pyrrolidin-2-ylmethyl]-1H-indol-3-yl}carbonyl)-7H-spiro[furo[3,4-b]pyridine-5,4'-piperidine]dihydrochloride

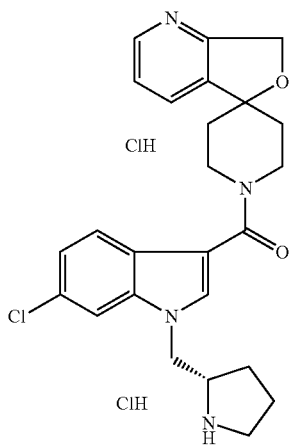

A solution of 0.19 g (0.34 mmol) tert-butyl (2S)-2-{[6-chloro-3-(1'H,7H-spiro[furo[3,4-b]pyridine-5,4'-piperidin]-1'-ylcarbonyl)-1H-indol-1-yl]methyl}pyrrolidine-1-carboxylate in 2.8 ml of a 1.25 M solution of hydrochloric acid (3.5 mmol) in methanol was stirred at 50° C. for 15 min. The reaction mixture was concentrated to dryness to give the title compound (0.18 g; 100%) as an off-white solid.
MS m/e (%): 451 (M+H$^+$, 100).

Example 4

1'-[(6-Chloro-1-{[(2S)-1-methylpyrrolidin-2-yl]methyl}-1H-indol-3-yl)carbonyl]-7H-spiro[furo[3,4-b]pyridine-5,4'-piperidine]

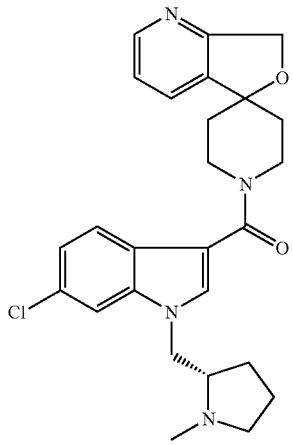

A solution of 0.15 g (0.29 mmol) 1'-({6-chloro-1-[(2S)-pyrrolidin-2-ylmethyl]-1H-indol-3-yl}carbonyl)-7H-spiro[furo[3,4-b]pyridine-5,4'-piperidine]dihydrochloride, 0.10 ml (0.72 mmol) triethylamine and 0.070 g (2.3 mmol) paraformaldehyde in 3 ml methanol was heated at reflux for 2 h. Cooling the reaction mixture to 0° C. using an ice-water bath was followed by addition of 0.030 g (0.43 mmol) sodium cyanoborohydride. The reaction mixture was stirred at room temperature for 16 h, quenched with water and diluted with 1 M aqueous sodium hydroxide solution. The aqueous layer was extracted with three portions of ethyl acetate. The combined organic layers were dried over sodium sulfate and concentrated in vacuo. The crude product was purified by flash column chromatography (aminopropyl-modified silica gel) to give the title compound (0.10 g; 77%) as an off-white solid.
MS m/e (%): 465 (M+H$^+$, 100).

Example 5

1'-{[6-Chloro-1-(3,5-difluorobenzyl)-1H-indol-3-yl]carbonyl}-7H-spiro[furo[3,4-b]pyridine-5,4'-piperidine]

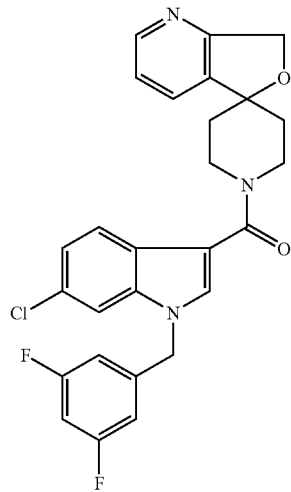

The title compound was obtained as a light yellow solid in 61% yield according to the amide coupling procedure described in general procedure IA.
Acid: 6-Chloro-1-(3,5-difluoro-benzyl)-1H-indole-3-carboxylic acid
Amine: 7H-Spiro[furo[3,4-b]pyridine-5,4'-piperidine]
MS m/e (%): 494 (M+H$^+$, 100).

Example 6

1'-[(6-Chloro-1H-indol-3-yl)carbonyl]-5H-spiro[furo[3,4-b]pyridine-7,4'-piperidine]

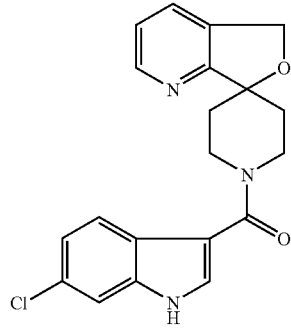

The title compound was obtained as an off-white solid in 69% yield according to the amide coupling procedure described in general procedure IA.
Acid: 6-Chloro-1H-indole-3-carboxylic acid
Amine: 5H-Spiro[furo[3,4-b]pyridine-7,4'-piperidine]
MS m/e (%): 368 (M+H$^+$, 100).

Example 7 tert-Butyl (2S)-2-{[6-chloro-3-(1'H,5H-spiro[furo[3,4-b]pyridine-7,4'-piperidin]-1'-ylcarbonyl)-1H-indol-1-yl]methyl}pyrrolidine-1-carboxylate

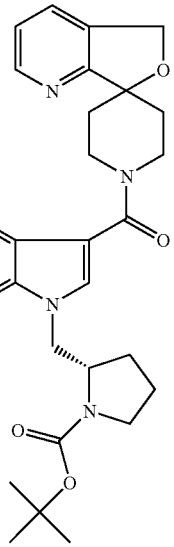

The title compound was obtained as a white solid in 57% yield according to the amide coupling procedure described in general procedure IB.
Acid: 1-((S)-1-tert-Butoxycarbonyl-pyrrolidin-2-ylmethyl)-6-chloro-1H-indole-3-carboxylic acid.
Amine: 5H-Spiro[furo[3,4-b]pyridine-7,4'-piperidine]
MS m/e (%): 551 (M+H$^+$, 100).

Example 8

1'-({6-Chloro-1-[(2S)-pyrrolidin-2-ylmethyl]-1H-indol-3-yl}carbonyl)-5H-spiro[furo[3,4-b]pyridine-7,4'-piperidine]dihydrochloride

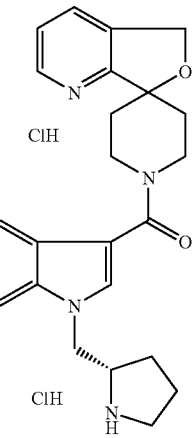

The title compound was obtained as an off-white solid in quantitative yield according to the procedure described for the preparation of 1'-({6-chloro-1-[(2S)-pyrrolidin-2-ylmethyl]-1H-indol-3-yl}carbonyl)-7H-spiro[furo[3,4-b]pyridine-5,4'-piperidine]dihydrochloride using tert-butyl (2S)-2-{[6-chloro-3-(1'H,5H-spiro[furo[3,4-b]pyridine-7,4'-piperidin]-1'-ylcarbonyl)-1H-indol-1-yl]methyl}pyrrolidine-1-carboxylate instead of tert-butyl (2S)-2-{[6-chloro-3-(1'H,7H-Spiro[furo[3,4-b]pyridine-5,4'-piperidin]-1'-ylcarbonyl)-1H-indol-1-yl]methyl}pyrrolidine-1-carboxylate.

MS m/e (%): 451 (M+H⁺, 100).

Example 9

1'-[(6-Chloro-1-1{[(2S)-1-methylpyrrolidin-2-yl]methyl}-1H-indol-3-yl)carbonyl]-5H-spiro[furo[3,4-b]pyridine-7,4'-piperidine]

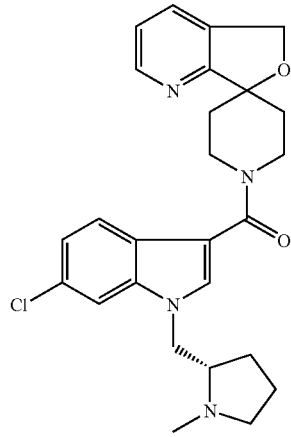

The title compound was obtained as a white solid in 84% yield according to the procedure described for the preparation of 1'-[(6-chloro-1-{[(2S)-1-methylpyrrolidin-2-yl]methyl}-1H-indol-3-yl)carbonyl]-7H-spiro[furo[3,4-b]pyridine-5,4'-piperidine] using 1'-({6-chloro-1-[(2S)-pyrrolidin-2-ylmethyl]-1H-indol-3-yl}carbonyl)-5H-spiro[furo[3,4-b]pyridine-7,4'-piperidine]dihydrochloride instead of 1'-({6-chloro-1-[(2S)-pyrrolidin-2-ylmethyl]-1H-indol-3-yl}carbonyl)-7H-spiro[furo[3,4-b]pyridine-5,4'-piperidine]dihydrochloride.

MS m/e (%): 465 (M+H⁺, 100).

Example 10

1'-[(6-Chloro-1H-indol-3-yl)carbonyl]-1H-spiro[furo[3,4-c]pyridine-3,4'-piperidine]

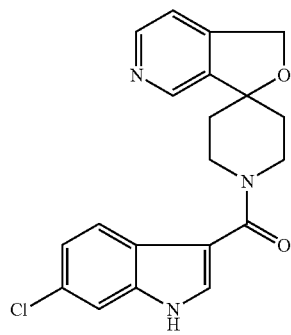

The title compound was obtained as an off-white solid in 67% yield according to the amide coupling procedure described in general procedure IA.
Acid: 6-Chloro-1H-indole-3-carboxylic acid
Amine: 1H-Spiro[furo[3,4-c]pyridine-3,4'-piperidine]
MS m/e (%): 368 (M+H⁺, 100).

Example 11 tert-Butyl (2S)-2-{[6-chloro-3-(1H, 1'H-spiro[furo[3,4-c]pyridine-3,4'-piperidin]-1'-ylcarbonyl)-1H-indol-1-yl]methyl}pyrrolidine-1-carboxylate

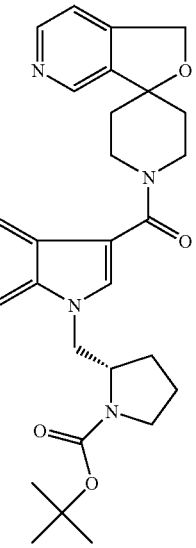

The title compound was obtained as a light yellow solid in 89% yield according to the amide coupling procedure described in general procedure IB.
Acid: 1-((S)-1-tert-Butoxycarbonyl-pyrrolidin-2-ylmethyl)-6-chloro-1H-indole-3-carboxylic acid
Amine: 1H-Spiro[furo[3,4-c]pyridine-3,4'-piperidine]
MS m/e (%): 551 (M+H⁺, 100).

Example 12

1'-({6-Chloro-1-[(2S)-pyrrolidin-2-ylmethyl]-1H-indol-3-yl}carbonyl)-1H-spiro[furo[3,4-c]pyridine-3,4'-piperidine]dihydrochloride

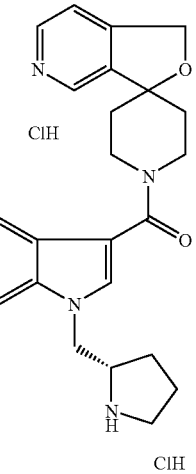

The title compound was obtained as a light yellow solid in 94% yield according to the procedure described for the preparation of 1'-({6-chloro-1-[(2S)-pyrrolidin-2-ylmethyl]-1H-indol-3-yl}carbonyl)-7H-spiro[furo[3,4-b]pyridine-5,4'-piperidine]dihydrochloride using tert-butyl (2S)-2-{[6-chloro-3-(1H,1'H-spiro[furo[3,4-c]pyridine-3,4'-piperidin]-1'-ylcarbonyl)-1H-indol-1-yl]methyl}pyrrolidine-1-carboxylate instead of tert-butyl (2S)-2-{[6-chloro-3-(1'H,7H-spiro[furo[3,4-b]pyridine-5,4'-piperidin]-1'-ylcarbonyl)-1H-indol-1-yl]methyl}pyrrolidine-1-carboxylate.

MS m/e (%): 451 (M+H+, 100).

Example 13

1'-[(6-Chloro-1-{[(2S)-1-methylpyrrolidin-2-yl]methyl}-1H-indol-3-yl)carbonyl]-1H-spiro[furo[3,4-c]pyridine-3,4'-piperidine]

The title compound was obtained as a white solid in 60% yield according to the procedure described for the preparation of 1'-[(6-chloro-1-{[(2S)-1-methylpyrrolidin-2-yl]methyl}-1H-indol-3-yl)carbonyl]-7H-spiro[furo[3,4-b]pyridine-5,4'-piperidine] using 1'-({6-chloro-1-[(2S)-pyrrolidin-2-ylmethyl]-1H-indol-3-yl}carbonyl)-1H-spiro[furo[3,4-c]pyridine-3,4'-piperidine]dihydrochloride instead of 1'-({6-chloro-1-[(2S)-pyrrolidin-2-ylmethyl]-1H-indol-3-yl}carbonyl)-7H-spiro[furo[3,4-b]pyridine-5,4'-piperidine] dihydrochloride.

MS m/e (%): 465 (M+H+, 100).

The invention claimed is:

1. A compound of the general formula (I)

wherein
U—V is —CH=CH—, or
U—V is —CH$_2$—CH$_2$—,
one of the variables W, X, Y and Z are nitrogen, the remaining variables being CR$^8$;
R$^1$ is H,
C$_{1-12}$-alkyl, optionally substituted with CN or OH,
C$_{1-6}$-haloalkyl,
C$_{2-12}$-alkenyl,
—(CR$^i$R$^{ii}$)$_m$—R$^a$,
wherein R$^i$ and R$^{ii}$ are independently from each other H, methyl, or ethyl;
wherein m is from 0 to 4;
wherein R$^a$ is
phenyl, 5- to 6-membered heteroaryl, 3- to 7-membered heterocycloalkyl or 3 to 7-membered cyloalkyl, which are optionally substituted with one or more A,
—NR$^b$R$^c$, wherein R$^b$ and R$^c$ are each independently
hydrogen,
hydroxy,
C$_{1-6}$-alkyl,
—S(O)$_2$—C$_{1-6}$-alkyl, or
—C(O)—C$_{1-6}$-alkyl,
—(CR$^{iii}$R$^{iv}$)$_n$—C(O)R$^d$,
wherein R$^{iii}$ and R$^{iv}$ are independently from each other H, methyl, or ethyl;
wherein n is from 0 to 4;
wherein R$^d$ is
C$_{1-6}$-alkoxy,
—NR$^e$R$^f$, wherein R$^e$ and R$^f$ are each independently
hydrogen,
C$_{1-6}$-alkyl, or
—(C$_{2-6}$-alkylene)-NR$^g$R$^h$; wherein R$^g$ and R$^h$ are each independently hydrogen, C$_{1-6}$-alkyl, or —C(O)O—C$_{1-6}$-alkyl,
phenyl, 5- to 6-membered heteroaryl, 3- to 7-membered heterocycloalkyl or 3 to 7-membered cyloalkyl, which are optionally substituted with one or more A,
—S(O)$_2$-phenyl, wherein phenyl is optionally substituted with one or more halo,
C$_{1-6}$-haloalkyl, C$_{1-6}$-alkoxy, C$_{1-6}$-haloalkoxy, nitro, hydroxy or cyano;
—S(O)$_2$—C$_{1-6}$-alkyl,
—S(O)$_2$N(C$_{1-6}$-alkyl)$_2$,
—S(O)$_2$NH(C$_{1-6}$-alkyl);
A is halo, C$_{1-6}$-alkyl, C$_{1-6}$-haloalkyl, C$_{1-6}$-hydroxyalkyl, C$_{1-6}$-cyanoalkyl, C$_{1-6}$-alkoxy, C$_{1-6}$-haloalkoxy, —S(O)$_{0-2}$C$_{1-6}$-alkyl, nitro, hydroxy, cyano, —(C$_{1-6}$-alkylene)-O—C$_{1-6}$-alkyl, —(C$_{1-6}$-alkylene)-O—C$_{1-6}$-haloalkyl, —(C$_{1-6}$-alkylene)-OR''', —C(O)OC$_{1-6}$-alkyl, —C(O)C$_{1-6}$-alkyl, —C(O)OR''', —C(O)R''', —C(O)NR'R'', —S(O)$_2$NR'R'', —(CH$_2$)$_x$—NR'R'', —(CH$_2$)$_x$—NR'C(O)—C$_{1-6}$-alkyl, —(CH$_2$)$_x$—NR'S(O)$_2$—C$_{1-6}$-alkyl, —(CH$_2$)$_x$—C$_{3-6}$-cycloalkyl, —(CH$_2$)$_x$—R''',
wherein x is from 0 to 4,
R' and R'' are each independently H or C$_{1-6}$-alkyl, or
R' and R'' together with the nitrogen to which they are bound form a 5 or 6-membered heterocycle comprising one or two heteroatoms selected from N, O and S, and
R''' is phenyl or 5- to 6-membered heteroaryl, optionally substituted with one, two, or three halo, C$_{1-6}$-haloalkyl, C$_{1-6}$-alkyl, or C$_{1-6}$-alkoxy, $R^2$ is hydrogen,
- $C_{1-6}$-alkyl,
- —C(O)R", wherein R" is
  - $C_{1-6}$-alkyl,
  - 3 to 7-membered heterocycloalkyl, optionally substituted with one, two or three $C_{1-6}$-alkyl, —C(O)O—$C_{1-6}$-alkyl, or —S(O)$_2$—$C_{1-6}$-alkyl,
  - NR$^j$R$^k$, wherein R$^j$ and R$^k$ are each independently
    - hydrogen,
    - $C_{1-6}$-alkyl,
    - —(C$_{2-6}$-alkylene)-NR$^l$R$^m$; wherein R$^l$ and R$^m$ are each independently hydrogen, $C_{1-6}$-alkyl, or —C(O)O—$C_{1-6}$-alkyl;

$R^3$, $R^4$, $R^5$, $R^6$ are each independently hydrogen, halo, $C_{1-6}$-alkyl, halo-$C_{1-6}$-alkyl, $C_{1-6}$-alkoxy or halo-$C_{1-6}$-alkoxy;

or $R^1$ and $R^6$ together with the indole ring to which they are attached form a 6 membered heterocycle which is optionally substituted with residues selected from =O, C(O)O—$C_{1-6}$-alkyl and $C_{1-6}$-alkyl;

$R^7$ is hydrogen or $C_{1-6}$-alkyl;

$R^8$ is hydrogen, halo, methyl, methoxy, $CF_3$, or $OCF_3$;

wherein 5- to 6-membered heteroaryl is selected from the group consisting of pyrrolyl, pyrazolyl, imidazolyl, furanyl, thiophenyl, oxazolyl, isoxazolyl, thiazolyl, isothiazolyl, pyridinyl, pyrimidinyl, pyrazinyl, and pyridazinyl; and 3- to 7-membered heterocycloalkyl is selected from the group consisting of oxiranyl, thiiranyl, aziridinyl, oxetanyl, azetidinyl, tetrahydro-furanyl, tetrahydro-thiophenyl, pyrrolidinyl, pyrazolidinyl, imidazolidinyl, oxazidinyl, isoxazidinyl, thiazolidinyl, isothiazolidinyl, piperidinyl, piperazidinyl, morpholinyl, and tetrahydropyranyl;

or a pharmaceutically acceptable salt thereof.

2. A compound of claim 1, wherein
$R^1$ is H,
- $C_{2-6}$-alkyl, optionally substituted with CN or OH,
- $C_{1-6}$-haloalkyl,
- —(CR$^i$R$^{ii}$)$_m$—R$^a$,
  - wherein R$^i$ and R$^{ii}$ are independently from each other H, methyl, or ethyl;
  - wherein m is from 0 to 4;
  - wherein R$^a$ is
    - phenyl, 5- to 6-membered heteroaryl, 3- to 7-membered heterocycloalkyl or 3 to 7-membered cyloalkyl, which are optionally substituted with one or more A, or
    - —NR$^b$R$^c$, wherein R$^b$ and R$^c$ are each independently hydrogen, $C_{1-6}$-alkyl, —S(O)$_2$—$C_{1-6}$-alkyl, or —C(O)—$C_{1-6}$-alkyl,
- —(CR$^{iii}$R$^{iv}$)$_n$—C(O)R$^d$,
  - wherein R$^{iii}$ and R$^{iv}$ are independently from each other H, methyl, or ethyl;
  - wherein n is from 0 to 4;
  - wherein R$^d$ is
    - $C^{1-6}$-alkoxy,
    - —NR$^e$R$^f$, wherein R$^e$ and R$^f$ are each independently
      - hydrogen,
      - $C_{1-6}$-alkyl, or
      - —(C$_{2-6}$-alkylene)-NR$^g$R$^h$; wherein R$^g$ and R$^h$ are each independently hydrogen, $C_{1-6}$-alkyl, or —C(O)O—$C_{1-6}$-alkyl, or
      - phenyl, 5- to 6-membered heteroaryl, 3- to 7-membered heterocycloalkyl or 3 to 7-membered cyloalkyl, which are optionally substituted with one or more A,
- —S(O)$_2$—$C_{1-6}$-alkyl,
- —S(O)$_2$N(C$_{1-6}$-alkyl)$_2$, or
- —S(O)$_2$NH(C$_{1-6}$-alkyl);

A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —S(O)$_{0-2}$C$_{1-6}$-alkyl, nitro, hydroxy, cyano, —(C$_{1-6}$-alkylene)-O—C$_{1-6}$-alkyl, —(C$_{1-6}$-alkylene)-O—C$_{1-6}$-haloalkyl, —(C$_{1-6}$-alkylene)-OR''', —C(O)OC$_{1-6}$-alkyl, —C(O)OR''', —C(O)R''', —C(O)NR'R'', —S(O)$_2$NR'R'', —(CH$_2$)$_x$—NR'R'', —(CH$_2$)$_x$—NR'C(O)—$C_{1-6}$-alkyl, —(CH$_2$)$_x$—NR'S(O)$_2$—$C_{1-6}$-alkyl, —(CH$_2$)$_x$—$C_{3-6}$-cycloalkyl, or —(CH$_2$)$_x$—R''',
wherein x is from 0 to 4, R' and R" are each independently H or $C_{1-6}$-alkyl, or R' and R" together with the nitrogen to which they are bound form a 5 or 6-membered heterocycle comprising one or two heteroatoms selected from N, O and S, and R''' is phenyl or 5- to 6-membered heteroaryl, optionally substituted with one, two, or three halo, $C_{1-6}$-haloalkyl, $C_{1-6}$-alkyl, or $C_{1-6}$-alkoxy wherein 5- to 6-membered heteroaryl is selected from the group consisting of pyrrolyl, pyrazolyl, imidazolyl, furanyl, thiophenyl, oxazolyl, isoxazolyl, thiazolyl, isothiazolyl, pyridinyl, pyrimidinyl, pyrazinyl, and pyridazinyl; and 3- to 7-membered heterocycloalkyl is selected from the group consisting of oxiranyl, thiiranyl, aziridinyl, oxetanyl, azetidinyl, tetrahydro-furanyl, tetrahydro-thiophenyl, pyrrolidinyl, pyrazolidinyl, imidazolidinyl, oxazidinyl, isoxazidinyl, thiazolidinyl, isothiazolidinyl, piperidinyl, piperazidinyl, morpholinyl, and tetrahydropyranyl.

3. The compound of claim 1, wherein $R^1$, $R^2$, $R^3$, $R^4$, $R^5$, and $R^6$ are not simultaneously hydrogen.

4. The compound of claim 1, wherein $R^1$ is hydrogen.

5. The compound of claim 1, wherein $R^1$ is $C_{1-12}$-alkyl, optionally substituted with CN or OH.

6. The compound of claim 1, wherein $R^1$ is $C_{1-6}$-haloalkyl or $C_{2-12}$Alkenyl.

7. The compound of claim 1, wherein $R^1$ is S(O)$_2$-phenyl, wherein phenyl is optionally substituted with one or more halo, $C_{1-6}$-haloalkyl, $C_{1-6}$-alkyl, $C_{1-6}$-alkoxy, $C_{1-6}$-haloalkoxy, nitro, hydroxyl or cyano.

8. The compound of claim 1, wherein $R^1$ is —S(O)$_2$—C$_{1-6}$-alkyl, —S(O)$_2$N(C$_{1-6}$-alkyl)$_2$, or —S(O)$_2$NH(C$_{1-6}$-alkyl).

9. The compound of claim 1, wherein
A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, $C_{1-6}$-thioalkyl, —S(O)$_2$—C$_{1-6}$-alkyl, cyano, —CH$_2$OCH$_3$, —C(O)O—$C_{1-6}$-alkyl, —C(O)NR'R'', —S(O)$_2$NR'R'', —NR'C(O)—$C_{1-6}$-alkyl, —NR'S(O)$_2$—$C_{1-6}$-alkyl, benzyl, or phenyl
wherein R' and R" are each independently H or $C_{1-6}$-alkyl.

10. The compound of claim 1, wherein $R^2$ is hydrogen or $C_{1-6}$-alkyl.

11. The compound of claim 1, wherein $R^3$, $R^4$, $R^5$, and $R^6$ are hydrogen.

12. The compound of claim 1, wherein $R^3$, $R^4$, $R^5$, and $R^6$ are each independently hydrogen, halo, $C_{1-6}$-alkyl, $C_{1-6}$-haloalkyl, $C_{1-6}$-alkoxy, or $C_{1-6}$-haloalkoxy.

13. The compound of claim 1, wherein $R^4$ is hydrogen, Cl, F, or methyl.

14. The compound of claim 1, wherein $R^5$ is hydrogen, halo, $CF_3$, methoxy, or —$OCF_3$.

15. The compound of claim 1, wherein $R^3$ and $R^6$ is hydrogen, $R^4$ is hydrogen, F, Cl, or methyl, and $R^5$ is halo, $CF_3$, methoxy, or $OCF_3$.

16. The compound of claim 1, wherein $R^7$ is hydrogen or $C_{1-6}$-alkyl.

17. The compound of claim 1, wherein $R^8$ is hydrogen, halo, methyl, methoxy, $CF_3$, or $OCF_3$.

18. The compound of claim 1, wherein
    W is N, X is CH, Y is CH, and Z is CH,
    W is CH, X is N, Y is CH, and Z is CH,
    W is CH, X is CH, Y is N, and Z is CH, or
    W is CH, X is CH, Y is CH, and Z is N.

19. The compound of formula (I) according to claim 6, wherein U—V is —CH=CH—.

20. A pharmaceutical composition comprising a therapeutically effective amount of a compound of formula I

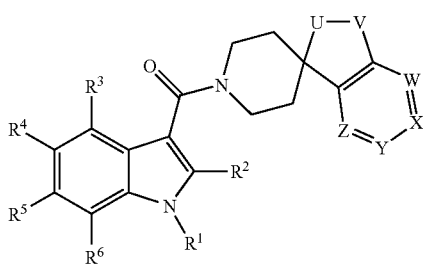

wherein
U—V is —CH=CH—, or
U—V is —$CH_2$—$CH_2$—,
one of the variables W, X, Y and Z are nitrogen, the remaining variables being $CR^8$;
$R^1$ is H,
    $C_{1-12}$-alkyl, optionally substituted with CN or OH,
    $C_{1-6}$-haloalkyl,
    $C_{2-12}$-alkenyl,
    —$(CR^iR^{ii})_m$—$R^a$,
        wherein $R^i$ and $R^{ii}$ are independently from each other H, methyl, or ethyl;
        wherein m is from 0 to 4;
        wherein $R^a$ is
            phenyl, 5- to 6-membered heteroaryl, 3- to 7-membered heterocycloalkyl or 3 to 7-membered cyloalkyl, which are optionally substituted with one or more A, or
            —$NR^bR^c$, wherein $R^b$ and $R^c$ are each independently
                hydrogen,
                hydroxy,
                $C_{1-6}$-alkyl,
                —$S(O)_2$—$C_{1-6}$-alkyl, or
                —C(O)—$C_{1-6}$-alkyl,
    —$(CR^{iii}R^{iv})_n$—$C(O)R^d$,
        wherein $R^{iii}$ and $R^{iv}$ are independently from each other H, methyl, or ethyl;
        wherein n is from 0 to 4;
        wherein $R^d$ is
            $C_{1-6}$-alkoxy,
            —$NR^eR^f$, wherein $R^e$ and $R^f$ are each independently
                hydrogen,
                $C_{1-6}$-alkyl, or
    —$(C_{2-6}$-alkylene)-$NR^gR^h$; wherein $R^g$ and $R^h$ are each independently hydrogen, $C_{1-6}$-alkyl, or —C(O)O—$C_{1-6}$-alkyl, or
    phenyl, 5- to 6-membered heteroaryl, 3- to 7-membered heterocycloalkyl or 3 to 7-membered cyloalkyl, which are optionally substituted with one or more A,
        —$S(O)_2$-phenyl, wherein phenyl is optionally substituted with one or more halo,
        $C_{1-6}$-haloalkyl, $C_{1-6}$-alkoxy, $C_{1-6}$-haloalkoxy, nitro, hydroxy or cyano;
    —$S(O)_2$—$C_{1-6}$-alkyl,
    —$S(O)_2N(C_{1-6}$-alkyl$)_2$, or
    —$S(O)_2NH(C_{1-6}$-alkyl);
A is halo, $C_{1-6}$-alkyl, $C_{1-6}$-haloalkyl, $C_{1-6}$-hydroxyalkyl, $C_{1-6}$-cyanoalkyl, $C_{1-6}$-alkoxy, $C_{1-6}$-haloalkoxy, —$S(O)_{0-2}C_{1-6}$-alkyl, nitro, hydroxy, cyano, —$(C_{1-6}$-alkylene)-O—$C_{1-6}$-alkyl, —$(C_{1-6}$-alkylene)-O—$C_{1-6}$-haloalkyl, —$(C_{1-6}$-alkylene)-OR''', —C(O)O$C_{1-6}$-alkyl, —C(O)OR''', —C(O)R''', —C(O)NR'R'', —$S(O)_2$NR'R'', —$(CH_2)_x$—NR'R'', —$(CH_2)_x$—NR'C(O)—$C_{1-6}$-alkyl, —$(CH_2)_x$—NR'S(O)$_2$—$C_{1-6}$-alkyl, —$(CH_2)_x$—$C_{3-6}$-cycloalkyl, or —$(CH_2)_x$—R''',
wherein x is from 0 to 4,
R' and R'' are each independently H or $C_{1-6}$-alkyl, or
R' and R'' together with the nitrogen to which they are bound form a 5 or 6-membered heterocycle comprising one or two heteroatoms selected from N, O and S, and
R''' is phenyl or 5- to 6-membered heteroaryl, optionally substituted with one, two, or three halo, $C_{1-6}$-haloalkyl, $C_{1-6}$-alkyl, or $C_{1-6}$-alkoxy,
$R^2$ is hydrogen, $C_{1-6}$-alkyl, or —$C(O)R^n$, wherein $R^n$ is $C_{1-6}$-alkyl, 3 to 7-membered heterocycloalkyl, optionally substituted with one, two or three $C_{1-6}$-alkyl, —C(O)O—$C_{1-6}$-alkyl, or —$S(O)_2$—$C_{1-6}$-alkyl, or $NR^jR^k$, wherein $R^j$ and $R^k$ are each independently
    hydrogen,
    $C_{1-6}$-alkyl, or
    —$(C_{2-6}$-alkylene)-$NR^lR^m$; wherein $R^l$ and $R^m$ are each independently hydrogen, $C_{1-6}$-alkyl, or —C(O)O—$C_{1-6}$-alkyl;
$R^3$, $R^4$, $R^5$, $R^6$ are each independently hydrogen, halo, $C_{1-6}$-alkyl, halo-$C_{1-6}$-alkyl, $C_{1-6}$-alkoxy or halo-$C_{1-6}$-alkoxy;
or $R^1$ and $R^6$ together with the indole ring to which they are attached form a 6 membered heterocycle which is optionally substituted with residues selected from =O, C(O)O—$C_{1-6}$-alkyl and $C_{1-6}$-alkyl;
$R^7$ is hydrogen or $C_{1-6}$-alkyl;
$R^8$ is hydrogen, halo, methyl, methoxy, $CF_3$, or $OCF_3$;
wherein 5- to 6-membered heteroaryl is selected from the group consisting of pyrrolyl, pyrazolyl, imidazolyl, furanyl, thiophenyl, oxazolyl, isoxazolyl, thiazolyl, isothiazolyl, pyridinyl, pyrimidinyl, pyrazinyl, and pyridazinyl; and
3- to 7-membered heterocycloalkyl is selected from the group consisting of oxiranyl, thiiranyl, aziridinyl, oxetanyl, azetidinyl, tetrahydro-furanyl, tetrahydro-thiophenyl, pyrrolidinyl, pyrazolidinyl, imidazolidinyl, oxazidinyl, isoxazidinyl, thiazolidinyl, isothiazolidinyl, piperidinyl, piperazidinyl, morpholinyl, and tetrahydropyranyl;
or a pharmaceutically acceptable salt thereof.

* * * * *